US012661442B2

(12) United States Patent
Norton et al.

(10) Patent No.: US 12,661,442 B2
(45) Date of Patent: Jun. 23, 2026

(54) ASPIRATION CATHETER SYSTEMS

(71) Applicant: JUPITER ENDOVASCULAR INC.,
Menlo Park, CA (US)

(72) Inventors: Jeffrey Norton, Emerald Hills, CA
(US); Tyler Middleton, San Francisco,
CA (US)

(73) Assignee: JUPITER ENDOVASCULAR INC.,
Menlo Park, CA (US)

( * ) Notice: Subject to any disclaimer, the term of this
patent is extended or adjusted under 35
U.S.C. 154(b) by 0 days.

(21) Appl. No.: 19/383,474

(22) Filed: Nov. 7, 2025

(65) Prior Publication Data

US 2026/0137853 A1      May 21, 2026

Related U.S. Application Data

(60) Provisional application No. 63/722,064, filed on Nov.
18, 2024.

(51) Int. Cl.
| | |
|---|---|
| *A61M 1/36* | (2006.01) |
| *A61B 17/22* | (2006.01) |
| *A61M 1/00* | (2006.01) |
| *A61M 1/34* | (2006.01) |
| *A61M 25/00* | (2006.01) |

(Continued)

(52) U.S. Cl.
CPC ............ *A61M 1/3627* (2013.01); *A61M 1/34*
(2013.01); *A61M 1/362264* (2022.05); *A61M*
*1/774* (2021.05); *A61M 25/0045* (2013.01);
*A61M 25/0155* (2013.01); *A61M 39/06*
(2013.01); *A61B 2017/22079* (2013.01); *A61M*
*2039/062* (2013.01); *A61M 2205/583*
(2013.01)

(58) Field of Classification Search
CPC .................. A61M 1/3627; A61M 1/34; A61M
1/362264; A61M 1/774; A61M 25/0045;
A61M 25/0155; A61M 39/06; A61M
2039/062; A61M 2205/583; A61M 1/79;
A61M 2202/0413; A61M 2202/0021;
A61M 2205/7545; A61M 1/60; A61M
1/602; A61M 1/604; A61M 1/61; A61M
1/62; A61B 2017/22079; A61B 17/22;
A61B 2017/2212; A61B 2217/005; A61B
2017/22038; A61B 17/12109; A61B
2017/22067; A61B 2017/2217; A61B
2017/1205; A61B 2018/0041; A61B
5/6852
See application file for complete search history.

(56) References Cited

U.S. PATENT DOCUMENTS

| | | | |
|---|---|---|---|
| 2004/0254525 A1* | 12/2004 | Uber, III | ............... A61M 5/007 604/67 |
| 2024/0016505 A1* | 1/2024 | Horowitz | ......... A61B 17/22031 |

(Continued)

FOREIGN PATENT DOCUMENTS

| | | | | |
|---|---|---|---|---|
| WO | WO-2009149691 A2 | * | 12/2009 | .............. A61M 1/60 |

*Primary Examiner* — Rebecca E Eisenberg
*Assistant Examiner* — Brandon W. Levy
(74) *Attorney, Agent, or Firm* — Squire Patton Boggs
(US) LLP

(57) ABSTRACT

Methods and apparatuses for blood clot aspiration.
Described are fluid management components and assem-
blies for blood clot extraction from a patient's body and for
filtering blood and recirculating blood back into the patient's
body.

20 Claims, 35 Drawing Sheets

(51) Int. Cl.
　　*A61M 25/01*　　　　(2006.01)
　　*A61M 39/06*　　　　(2006.01)

(56) References Cited

U.S. PATENT DOCUMENTS

2024/0024640 A1*　1/2024　Gomes ............... A61M 25/0102
2025/0222185 A1*　7/2025　Buck ....................... A61M 1/79

* cited by examiner 1308          1320

A

A

1308

1300

1985

1304

(section A-A')

RVOT
Strain

RA/RV
Strain

1220

2020

2020

1220

Sterile field

1700

1746

1700      1750

1760

1762

1752

1764

1754      1720

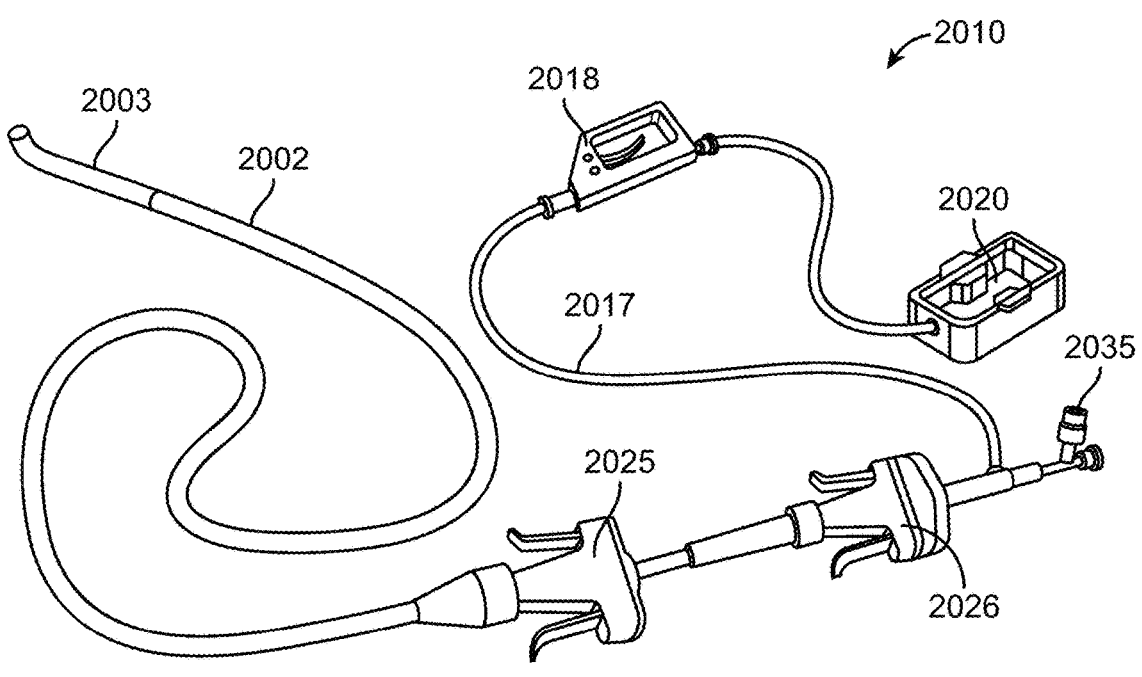
FIG. 20A
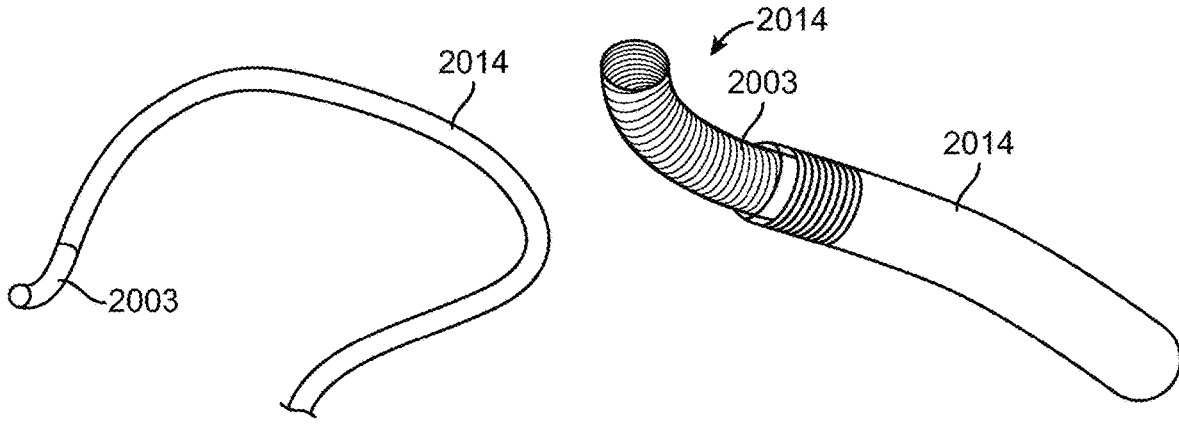
FIG. 20B
FIG. 20C

ASPIRATION CATHETER SYSTEMS

CROSS-REFERENCES TO RELATED APPLICATIONS

The present application claims the benefit of and priority to U.S. Provisional Patent Application No. 63/722,064, filed Nov. 18, 2024, the content of which is hereby incorporated by reference in its entity.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Blood clot material (e.g., thrombus) may be removed from vasculature using any of a number of procedures, including mechanical removal, hydraulics (pressurized fluid streams) and by aspiration. Generally, aspiration systems apply vacuum along a lumen of a catheter from a proximal low-pressure source (for example, a vacuum pump) to a distal opening of the catheter. Along the luminal path, systems typically incorporate features such as valves, gages, disconnects, flush ports, guidewire access ports, and filters, and other components for blood re-infusion.

In some cases, other, more difficult or complicated treatments, are required. For example, pulmonary embolism treatment may require thrombolytics, which may be expensive, may have potentially deadly complications, may require an ICU stay, and are not particularly effective for larger or older clots. In some cases, pulmonary embolism treatment may require surgery, which may be traumatic and expensive, including a sternotomy and bypass, and may require an extended stay in the hospital, and prolonged recovery.

In some cases, the blood clot material is filtered from the extracted blood and the filtered non-clotted blood is returned into the patient's vasculature. This minimizes blood loss while removing the clot material from the patient's blood. This blood return procedure may be done simultaneously with the clot aspiration process to provide a continuous blood flow. Such blood return procedures along with the clot removal procedures can require multiple steps that sometimes must be performed in a particular order.

There is a need for methods and apparatuses that may provide improved blood clot aspiration procedures, including safer and easier ways to managing fluids during blood clot aspiration procedures.

SUMMARY OF THE DISCLOSURE

Described herein are methods and apparatuses, including systems and devices, for cardiovascular treatments, and in particular for blood clot aspiration procedures. For example, described herein are various systems and components configured for safe extraction of clot material and improved fluid management during clot aspiration procedures. The systems include components for filtering the clot material from aspirated blood and return filtered blood back into the patient. The systems may include features that allow for easier management of the blood and other fluids (e.g., air, vacuum) during clot aspiration procedures, thereby allowing for safer overall procedures.

The systems described herein may be used in blood clot aspiration procedures performed in a vasculature of a subject. As used herein, vasculature may include any vascular region of the body, including, but not limited, regions of the heart, arteries, veins, capillaries, peripheral vasculature, and neurovascular structures. In general, the methods and apparatuses described herein are particularly useful for vascular indications, including cardiovascular, peripheral vascular, cerebrovascular, neurovascular, pulmonary vascular, thoracic vascular, abdominal vascular, lymphatic vascular, renal vascular, and/or genitourinary vascular indications.

The systems may include components configured to aspirate the blood clot material from the patient. For example, an aspiration catheter may include an elongate distal catheter portion that is adapted to be inserted and advanced through a patient's vasculature toward the clot material. The aspiration catheter may include a control that a user can use to control the suction applied within the vasculature. Such control may be on a handle at a proximal end of the aspiration catheter.

The system may include components that manage blood once it is removed from the patient's body. In some examples, the components may be adapted to filter clot material out of the blood and return the filtered blood back into the patient. The components may be connected by lines (e.g., tubing) configured to provide the flow of fluid (e.g., blood, air, vacuum) to and from the various components. Such components and lines may collectively form a blood return circuit for returning the aspirated blood to the patient.

The systems may include an aspiration catheter that is configured to aspirate blood, including clot material, from a patient's vasculature. A clot capture chamber may be configured to receive blood from an aspiration catheter and capture and contain at least some of the clot material from the aspirated blood. The clot capture chamber may include features that allow a user (e.g., doctor or assistant) to visualize and/or access the clot material and to easily handle the clot capture chamber. For example, the clot capture chamber may include a clot capture vent valve that is configured to allow venting of the clot capture chamber to an external atmosphere. The clot capture chamber may include a lid that is configured to automatically open, for example, when the clot capture chamber is vented. This allows the user to easily access a removable tray that captures the clot material, and which may need to be emptied or otherwise accessed. The clot capture chamber may include a latch that retains the lid in a closed position after the accessing the tray. The removable tray may have a perforated surface that is sloped to help reduce clogging and provide efficient flow of blood through the clot capture chamber.

The systems may include a reservoir that is configured to receive blood from the clot capture chamber and include a filter that is configured to filter the blood. The reservoir may include a window that allows a user to visualize a level of filtered blood contained within the reservoir. In some cases, the reservoir includes graduation marks on or near the window so that a user can easily determine a current amount of blood stored within the reservoir.

The systems may include a blood return syringe that is configured to receive filtered blood from the reservoir and to inject the filtered blood into the patient's vasculature. The blood return syringe may include a chamber (e.g., barrel) and a plunger that is used to pull the filtered blood into the chamber and to push the filtered blood into the patient.

The systems described herein may include a vent system that is adapted to efficiently vent one or more components of the system, for example, as part of a blood return circuit. The vent system may include a common vent line that is configured to fluidly couple the reservoir, the clot capture chamber and the blood return syringe. A syringe vent valve may allow venting of the blood return syringe to the common vent line to equalize a pressure among the blood return syringe, the clot capture chamber and the reservoir. A clot capture vent valve may allow venting of the clot capture chamber to an external atmosphere. As discussed herein, this common vent line configuration may allow a streamlined workflow for the user.

Any of the systems described herein may include a rigidizing aspiration sheath catheter. The rigidizing aspiration sheath catheters may be advanced with the subject's vasculature toward a target location (e.g., that includes a blood clot). The rigidizing aspiration sheath catheters may be advanced within the vasculature while in a flexible state, then rigidized into a rigid state once at the target location. The clot material may be aspirated through the rigidizing aspiration sheath catheter in the rigid state to remove the clot material from the vasculature. In some examples, an aspiration catheter may be inserted and advanced through the rigidizing aspiration sheath catheter to aspirate the clot material using the aspiration catheter. The rigidizing aspiration sheath catheters may be configured to apply aspiration (e.g., suction) directly through the lumen of the rigidizing aspiration sheath catheter and/or they may be configured to receive an aspiration catheter (which, in some examples, may or may not also be rigidizing).

The rigidizing aspiration sheath catheters may be rigidized by the application of pressure (negative and/or positive) within walls of the rigidizing aspiration sheath catheters. In some examples, the same suction (vacuum) line may be attached (swapped between) the aspiration catheter and the rigidizing aspiration sheath catheter. Alternatively in some examples, the suction may be applied to both the rigidizing aspiration sheath catheter and an aspiration catheter within the lumen of the rigidizing aspiration sheath catheter (e.g., around the aspiration catheter).

Also described herein are aspiration catheters (which may be rigidizing or non-rigidizing), a suction line, including an in-line vacuum activation valve and a clot capture chamber. All of some of these components may be used together, e.g., as part of system, or each of them may be used separately and may be configured to include elements of particular use in removing clot material.

The apparatuses and methods described herein may be used for aspiration of clot material from any region of the vasculature, including (but not limited to) pulmonary embolism, peripheral (e.g., arterial embolism), central (e.g., cerebral thrombus), etc., including treatment of stroke.

The aspiration of clots can involve removal of blood. The blood must be captured, and in some cases the blood must be returned to the patient. The present invention contemplates methods to capture, store and return blood to the patient. These include the use of filters and containers that are capable of separating blood in a sterile field. The system may also anticipate the use of standard cardiotomy reservoirs. Cardiotomy reservoirs are indicated for use in cardiopulmonary bypass circuits during surgery. Intended uses include an air-fluid separation chamber, a temporary storage reservoir for priming solutions, filtration of particulate materials (clots, blood cell aggregates, etc.). Design accommodations in the present system would allow these reservoirs to be uniquely adapted to an aspiration embolectomy system.

One or more of components of the systems described herein may be configured to remain within the sterile field while other components of the system may be configured to remain outside of the sterile field during a medical procedure. In cases where a rigidizing aspiration sheath catheter is used, the rigidizing aspiration sheath catheter may be positioned within the body and used for multiple introductions and removal steps, typically without requiring the use of a guidewire. Aspiration without a guidewire enables larger luminal area (and therefore greater suction), it reduces guidewire risks, and enables for smoother clot transit, because the clot does not need to shear relative to the wire. This may allow the system to be operated within the limited sterile filed during the entire procedure.

Any of the aspiration catheters and/or rigidizing aspiration sheath catheters described herein may include an atraumatic tip at the distal end of the aspiration catheters or rigidizing aspiration sheath catheter. For example, the distal end (tip) region may be formed of a relatively soft (e.g., low durometer) material and may be rounded.

A vacuum line for the aspiration catheter may include: a mating attachment at a distal end of vacuum line configured to lockingly engage with the mating attachment connector of the aspiration catheter. As mentioned, the mating attachment may be a universal attachment for coupling with one or more of the catheters of the system. For example, the mating attachment may include a bayonet-type attachment as well as one or more finger-grip regions enhancing the ease of use. The vacuum line may include vacuum tubing. Any of these apparatus may include a vacuum activation valve. This apparatus may be hand-triggered, comprising a handle and configured to open or close the vacuum line, wherein the hand-triggered vacuum activation valve is connected in-line with the mating attachment, wherein a proximal end of the vacuum line is further configured to couple to vacuum pump and blood collection chamber. This valve may be a roller mechanism that pinches the vacuum tubing locally.

In some examples the system includes a clot capture chamber that may be connected in-line with hand-triggered vacuum activation valve and may include a visualization chamber mounted above an exit port, wherein the exit port is connected to the proximal end region of the vacuum line. The clot capture chamber may include a removable tray within the visualization chamber. The removable tray may be sized to conform to an inner perimeter of the clot capture container. In some examples the clot capture chamber comprises a transparent lid, which may include one or more tabs. The tray may have a mesh size such that blood passes through, but clot does not. For example, the mesh may have a mesh size of between about 0.037 mm and about 6 mm (e.g., between about 0.05 mm and about 5 mm, between about 0.1 mm and about 4 mm, between about 0.2 mm and 3 mm, between about 0.3 mm and 2.5 mm, between about 0.5 mm and about 4 mm, between about 0.75 mm and about 4 mm, etc.).

As mentioned, any of these systems may include an aspiration catheter configured to be inserted through the central bore and into the lumen of the rigidizing aspiration sheath catheter, the aspiration catheter comprising a second mating attachment connector, wherein the mating attachment at the distal end of vacuum line is configured to lockingly engage with the second mating attachment connector or the first mating attachment connector. The aspiration catheter may comprise an aspiration lumen extending therethrough and an aspiration catheter hemostasis valve region at a proximal end.

In general, a method for removing clot material may include: aspirating blood with the blood clot material from a patient's vasculature using an aspiration catheter, wherein: a clot capture chamber receives the aspirated blood from the aspiration catheter and captures at least some of the blood clot material from the aspirated blood within the clot capture chamber; a reservoir receives blood from the clot capture chamber, wherein the reservoir includes a filter that is configured to filter the blood received from the clot capture chamber; opening a syringe vent valve to allow venting of a blood return syringe to a common vent line that fluidly couples the reservoir, the clot capture chamber and the blood return syringe, wherein opening the syringe vent valve equalizes a pressure among the blood return syringe, the clot capture chamber and the reservoir; drawing filtered blood into the blood return syringe from the reservoir while the syringe vent valve is open; and injecting the filtered blood into the patient's vasculature from the blood return syringe.

Any of these methods may include observing a clot material aspirated through the aspiration catheter within a window of a clot capture chamber connected in-line with hand-triggered vacuum activation valve.

As mentioned, these apparatuses may be used with or without a guidewire, either for the entire procedure or for the portion of the procedure following initially placing the rigidizing aspiration sheath catheter (e.g., rigidizing over-tube). For examples, advancing the rigidizing aspiration sheath catheter may include advancing the rigidizing aspiration sheath catheter without the use of a guidewire. In some examples advancing the rigidizing aspiration sheath catheter comprises advancing the aspiration catheter distally relative to the rigidizing aspiration sheath catheter in the rigid state and steering a distal end of the aspiration catheter. The method may further include advancing the rigidizing aspiration sheath catheter in the flexible state over the aspiration catheter and rigidizing the rigidizing aspiration sheath catheter. In some examples advancing the rigidizing aspiration sheath catheter comprises advancing the aspiration sheath catheter with an obturator within a lumen of the rigidizing aspiration sheath catheter.

Any of these apparatuses may be systems that also include one or more aspiration catheters. The aspiration catheter may also include an integrated hemostasis region (e.g., at a proximal end). The proximal ends of the rigidizing aspiration sheath catheters and the aspiration catheters may be adapted to interchangeably engage with a suction (aspiration) line. Any of the rigidizing aspiration sheath catheters may be steerable or may be steered by using an obturator and/or guidewire. In some cases the rigidizing aspiration sheath catheter include one or more distal steering regions that may be steered from the proximal end, e.g., by pulling on a tendon. In some cases the obturator configured to fit into the rigidizing aspiration sheath catheter may be steerable. In some cases the obturator adapted to fit snugly into the rigidizing aspiration sheath catheter may adapt the rigidizing aspiration sheath catheter for use with a guidewire (e.g., the obturator may include a guidewire lumen).

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 10A shows a schematic illustration of the system. FIG. 10B illustrates the system of FIG. 10A including the optional blood return circuit portion.

FIG. 20A-20C illustrate an example of an apparatus as described herein.

DETAILED DESCRIPTION

Described herein are methods and apparatuses (e.g., devices, systems, assemblies, etc.) for vascular (e.g., cardiovascular) treatment. These methods and apparatuses may be configured for removal of clot material (e.g., for clot capture) by aspiration. The systems may include components for aspirating blood clot material from a patient's body, filtering the blood from the clot material, and returning the filtered blood back into the patient's body. The components that filter and return the blood to the patient may be referred to as a blood return circuit. The systems may include features that provide real-time control and visualization of various components used during a clot aspiration procedure, including the blood return circuit, thereby providing a safer overall procedure.

Figure 1A:
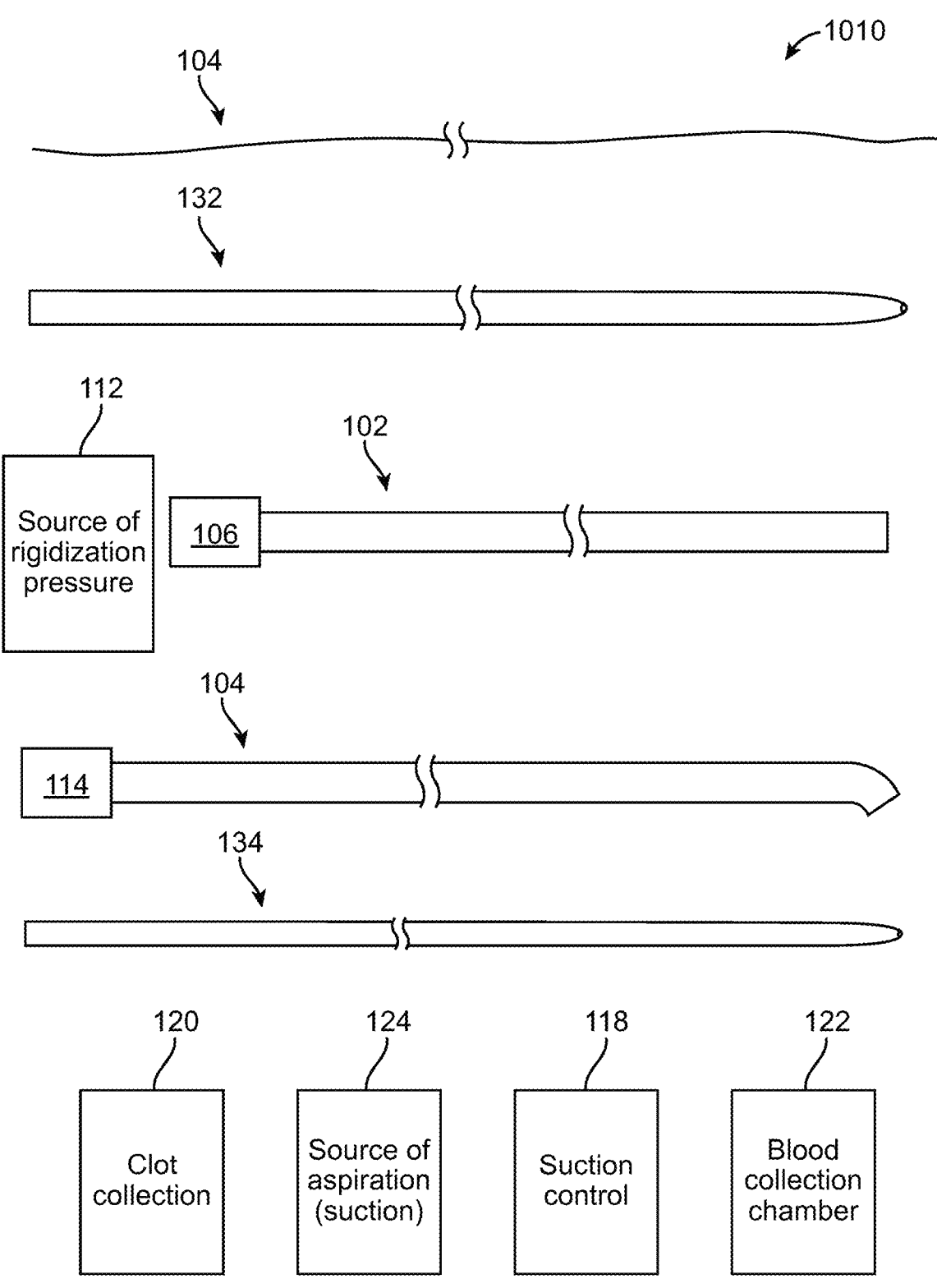
FIG. 1A shows one example of a system including a rigidizing aspiration sheath catheter apparatus as described herein.

In some examples the method and apparatuses described herein may include a vacuum line with one or more of: a hand-triggered vacuum activation valve and/or a clot capture chamber for visualizing and removing clot material aspirated by the system. FIG. 1A schematically illustrates one example of an apparatus (e.g., system), which in this example, includes a rigidizing aspiration sheath catheter 102 that includes a proximal region configured as a hemostasis valve region 106. The rigidizing aspiration sheath catheter 102 may be configured to be changed between a flexible state (flexible configuration) and a less flexible, e.g., rigid, state (rigid configuration). Any appropriate structure for rigidizing may be used, including in particular a layered structure that is rigidized by the application of positive and/or negative pressure. For example, these apparatuses may be configured as a rigidizing aspiration sheath catheter 102 configured to couple to a source of positive and/or negative pressure 112, e.g., through a port or inlet on the proximal end (which may be part of the hemostasis valve region or separate from it) to control the rigidity of the rigidizing aspiration sheath catheter 102. In some examples the rigidizing aspiration sheath catheter apparatus 102 has an elongate body comprising lumen extending therethrough. The elongate body may include layers, such as a rigidizing layer and a bladder layer that are configured to transition the elongate body between a flexible state and a rigid state by the application of pressure. As described in greater detail below, the bladder layer (e.g., "bladder") may be driven against (or allowed to move away from) the rigidizing layer to control the flexibility/stiffness of the elongate body. The rigidizing layer may comprise a plurality of overlapping filament lengths that are free to slide over each other in the more flexible state(s), but may the bladder layer may be driven against the rigidizing layer, and/or against a support layer (e.g., a reinforced layer) on an inner or an outer region of the elongate body, to rigidize the elongate body.

The rigidizing aspiration sheath catheter 102 may be used with one or more obturators 132. In FIG. 1A the obturator may be inserted into the rigidizing aspiration sheath catheter 102 over a guidewire 104 (which may be included with the apparatus 1010 or may be separately provided). This may allow the rigidizing aspiration sheath catheter 102 to be guided over a guidewire positioned in a body vessel. The obturator may be steerable or not. In general, the obturator may be flexible so that the combined obturator and rigidizing aspiration sheath catheter 102 (in the flexible configuration) may readily track over a guidewire. The obturator may be longer than the rigidizing aspiration sheath catheter 102 (e.g., by more than 1 cm (e.g., between 1 cm-20 cm, between 1 cm-30 cm, 1 cm-40 cm, etc. or any number therebetween) to allow tracking while avoiding "fishmouthing" over the rigidizing aspiration sheath catheter 102 distal end opening. The obturator may have an atraumatic tip. The obturator may have regions of different material properties (e.g., stiffnesses), such as described in PCTUS2022082141, filed Dec. 21, 2022, and herein incorporated by reference in its entirety.

The apparatus 1010 (e.g., system) in FIG. 1A may also include one or more aspiration catheters 104 that may also include a proximal hemostasis valve region. The aspiration catheter 104 may also be used with an obturator 134 that may be inserted through the aspiration catheter 104 and inserted through the rigidizing aspiration sheath catheter 102, e.g., in the rigid configuration. In some cases it may be beneficial for the distal tip region of the aspiration catheter 104 to be directional (e.g., bent, curved, etc.) in a fairly rigid bend, to allow for directional aspiration when extended from the rigid rigidizing aspiration sheath catheter 102. The aspiration catheter 104 may generally be configured to have a relatively high flexibility with a high torquability. The high torquability may allow the apparatus to be steered (directed) within the rigidizing aspiration sheath catheter 102 when extended distally of the distal end of the rigidizing aspiration sheath catheter 102, e.g., in the rigid configuration.

Other system components may include tubing (suction line) connecting the rigidizing aspiration sheath catheter 102 and/or aspiration catheter 104 to a source of aspiration 124. The rigidizing aspiration sheath catheter 102 and/or aspiration catheter 104 may be connected via a sealing connection to the suction line, which may be connected in-line to a clot collection chamber 120, and/or a suction (e.g., vacuum) activation valve, which may be activated to apply the suction to the rigidizing aspiration sheath catheter 102 and/or aspiration catheter 104. The apparatus may also include a blood collection chamber 122 before the source of aspiration 123 (e.g., suction pump). These components may be arranged between the rigidizing aspiration sheath catheter 102 and/or aspiration catheter 104 and the source of aspiration in any appropriate order.

Figure 1B:
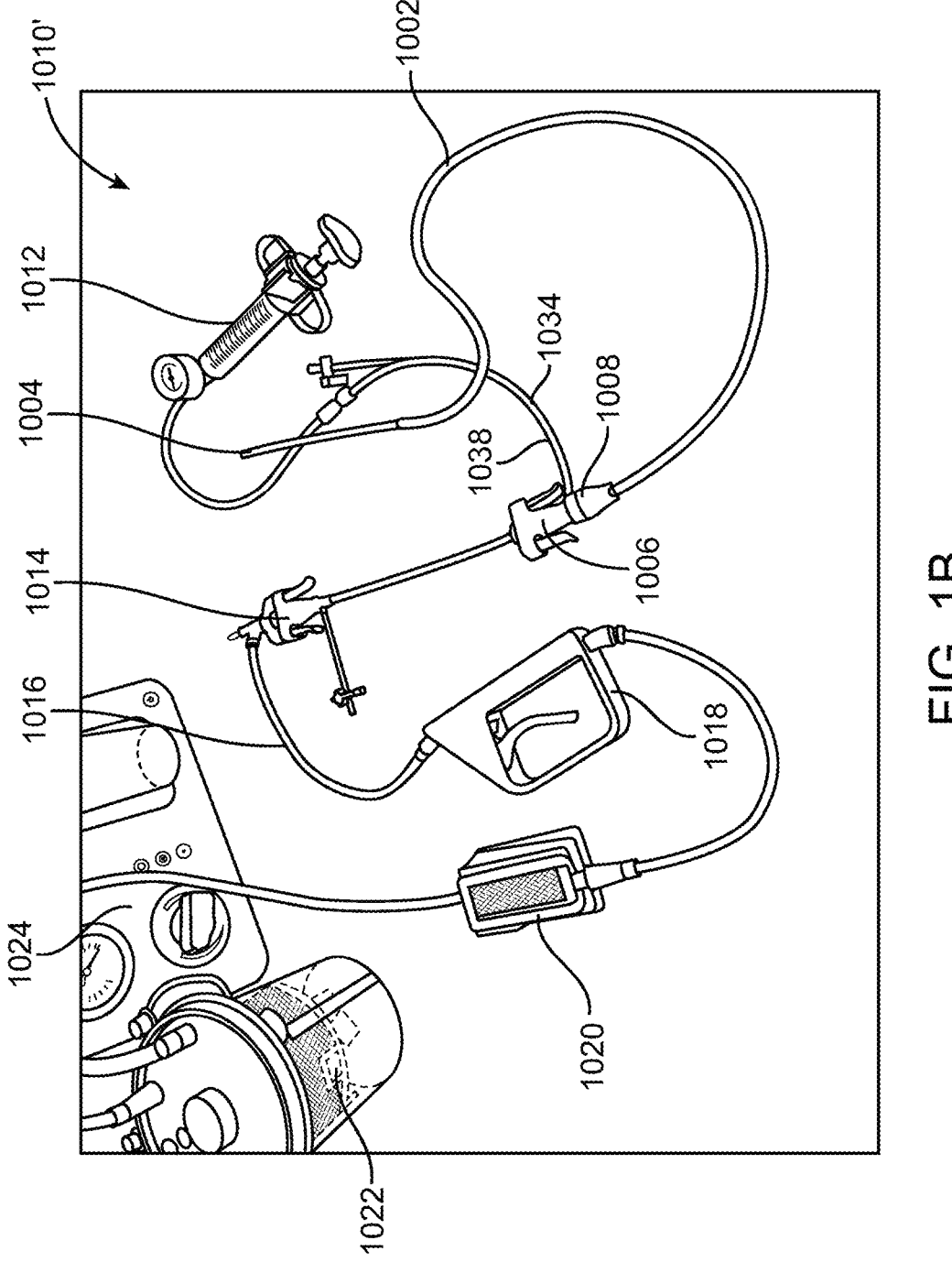
FIGS. 1B-1G show examples of a system and components of these systems as described herein.

For example, FIG. 1B illustrates an example of an apparatus (e.g., a system) for clot aspiration including these components. In FIG. 1B the system 1010' includes a rigidizing aspiration sheath catheter 1002 that is shown coupled to an insufflator 1012 to control transitioning between a rigid state and a flexible state. The aspiration system 1010' also include an aspiration catheter 1004. The dynamically rigidizing aspiration sheath catheter 1002 includes a hemostatic valve region 1006. The hemostatic valve region includes a connection 1008 to a pressure source (e.g., insufflator 1012). The aspiration catheter 1004 extends proximally from the hemostatic valve region to an aspiration catheter handle 1014. Through the aspiration catheter handle, the aspiration catheter comprises a connection to a tube or other elongate element 1016 that connects to a vacuum activation valve 1018. The tube 1016 extends proximally to a clot capture chamber 1020. A vacuum pump 1024 is positioned at a proximal portion of the aspiration lumen 1016 and blood collection container 1022.

Figures 1C, 1D:
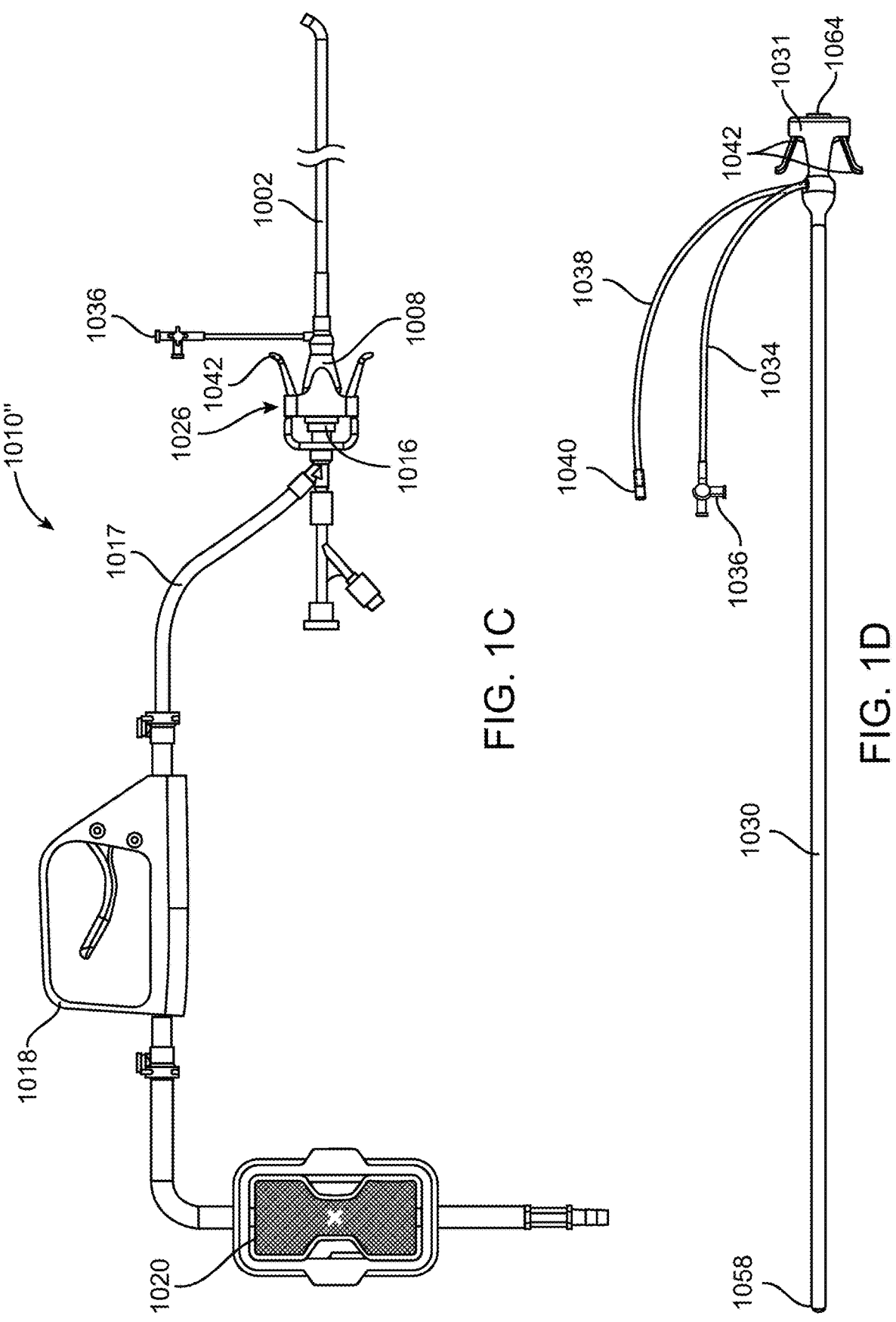

FIG. 1C shows another example of a portion of a system 1010" as described herein, including an aspiration catheter 1002 with an integrated hemostatic valve 1026 and a flush port 1036. The aspiration catheter is shown locking coupled to a mating attachment 1016 at a distal end of vacuum line.

The mating attachment is configured to couple to a mating attachment connector on the distal end of the aspiration catheter for making a quick connection to the suction line 1017. A hand-triggered vacuum activation valve 1018 is shown connected in-line with the vacuum line and may be easily used to turn on/off suction through the apparatus. The vacuum line is also connected to a clot capture chamber 1020, described in greater detail below.

Figures 1E, 1F, 1G:
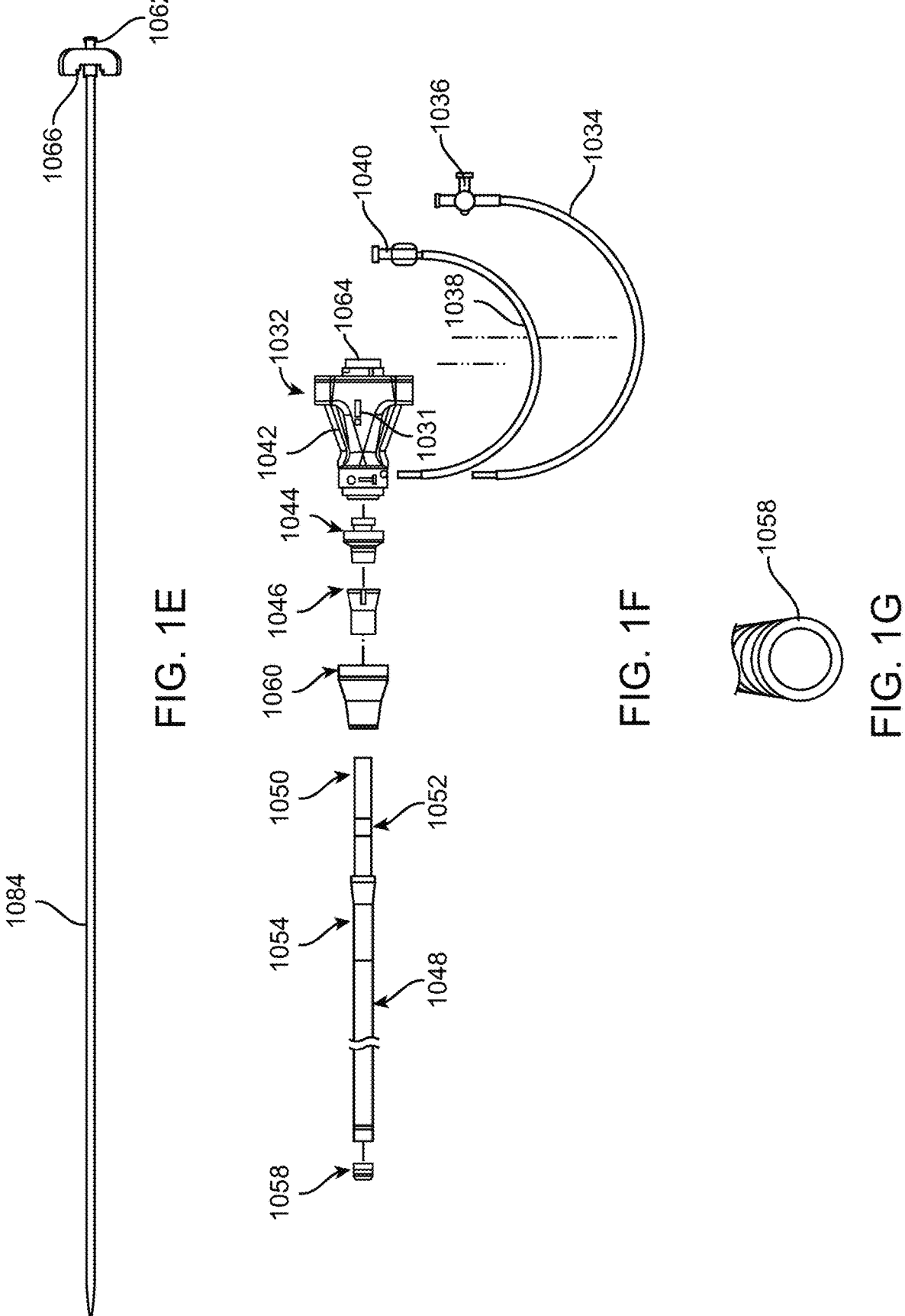

FIGS. 1D-1G show embodiments of components of an aspiration system (e.g., like those shown in FIG. 1B). Referring now to FIGS. 1D and 1F, the system may include a rigidizing aspiration sheath catheter 1030 including a hemostatic seal region 1031 at a proximal end. The hemostatic seal region 1032 comprises a body 1031. The seal in this example also includes a tube or elongate element 1034 connecting to a flush port 1036. In some embodiments, the flush port can comprise a luer type adapter. The hemostatic seal region 1032 also includes a tube or elongate element 1038 with a connector 1040 at its proximal end for connection to a pressure source (e.g., an insufflator). The connector may be a luer type connector.

Figure 7A:
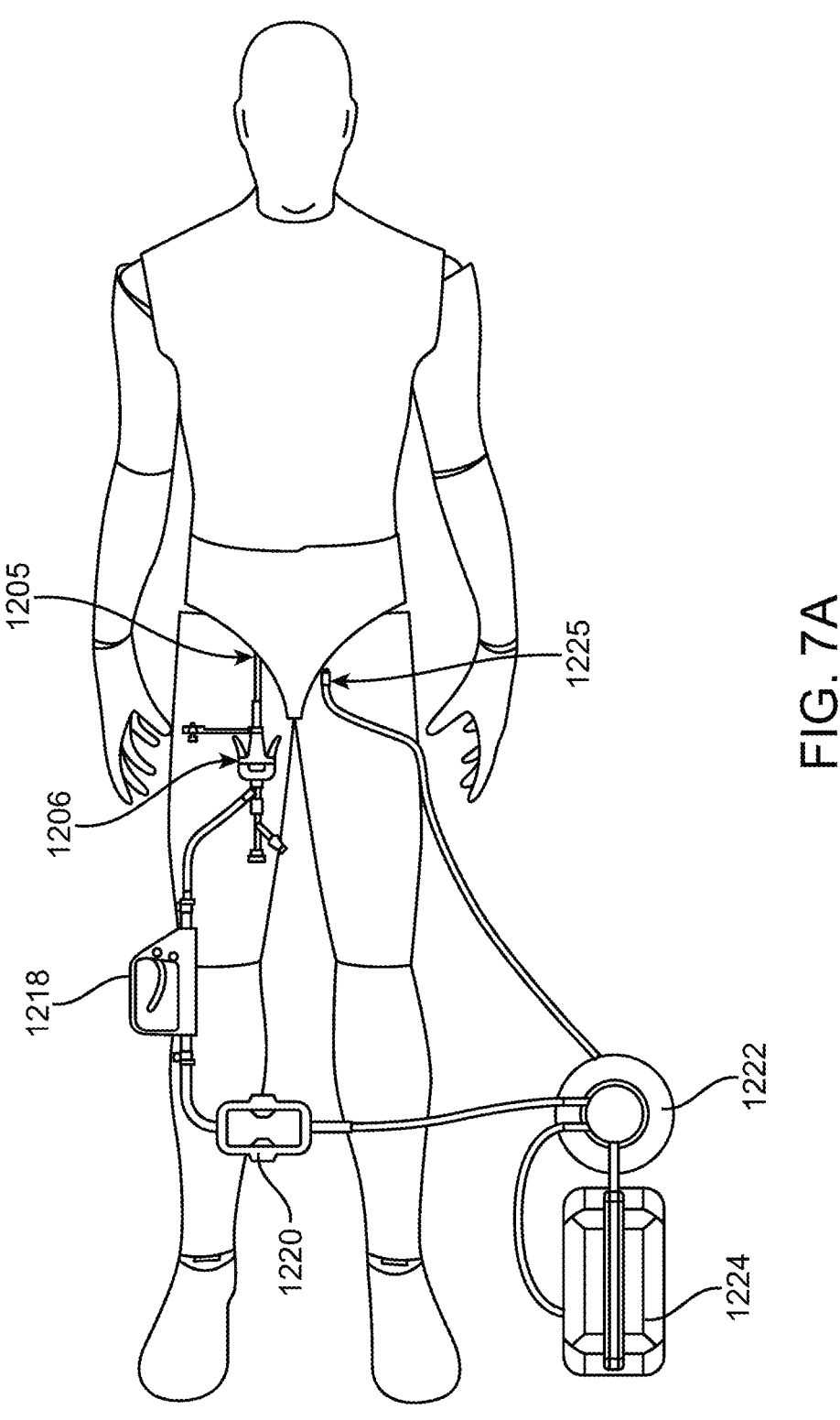
FIGS. 7A-7B illustrate an example of a system including a rigidizing aspiration sheath catheter configured with a blood return circuit having separate access and return sites on the body, as described herein.
Figure 7B:
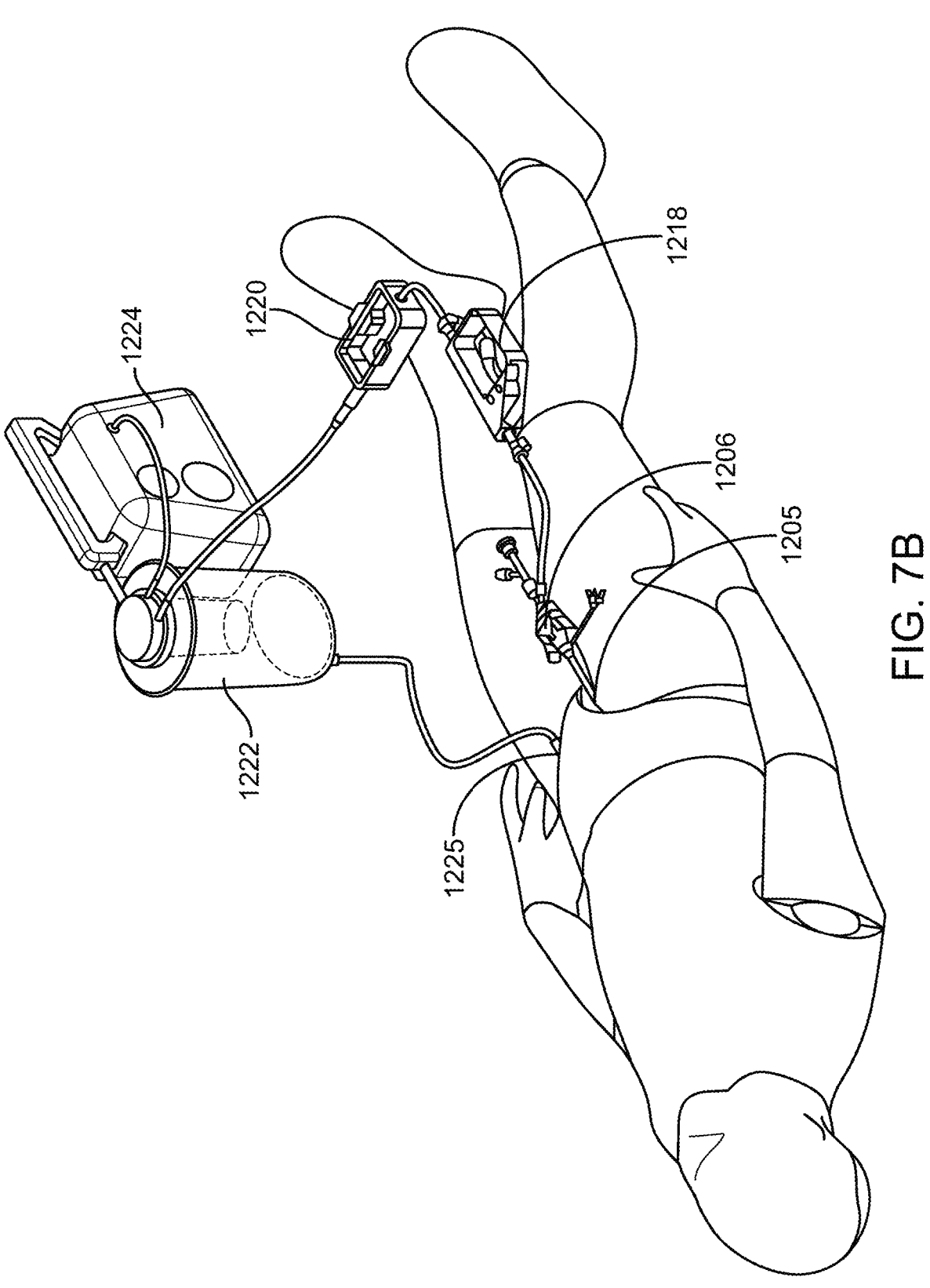
Figure 8A:
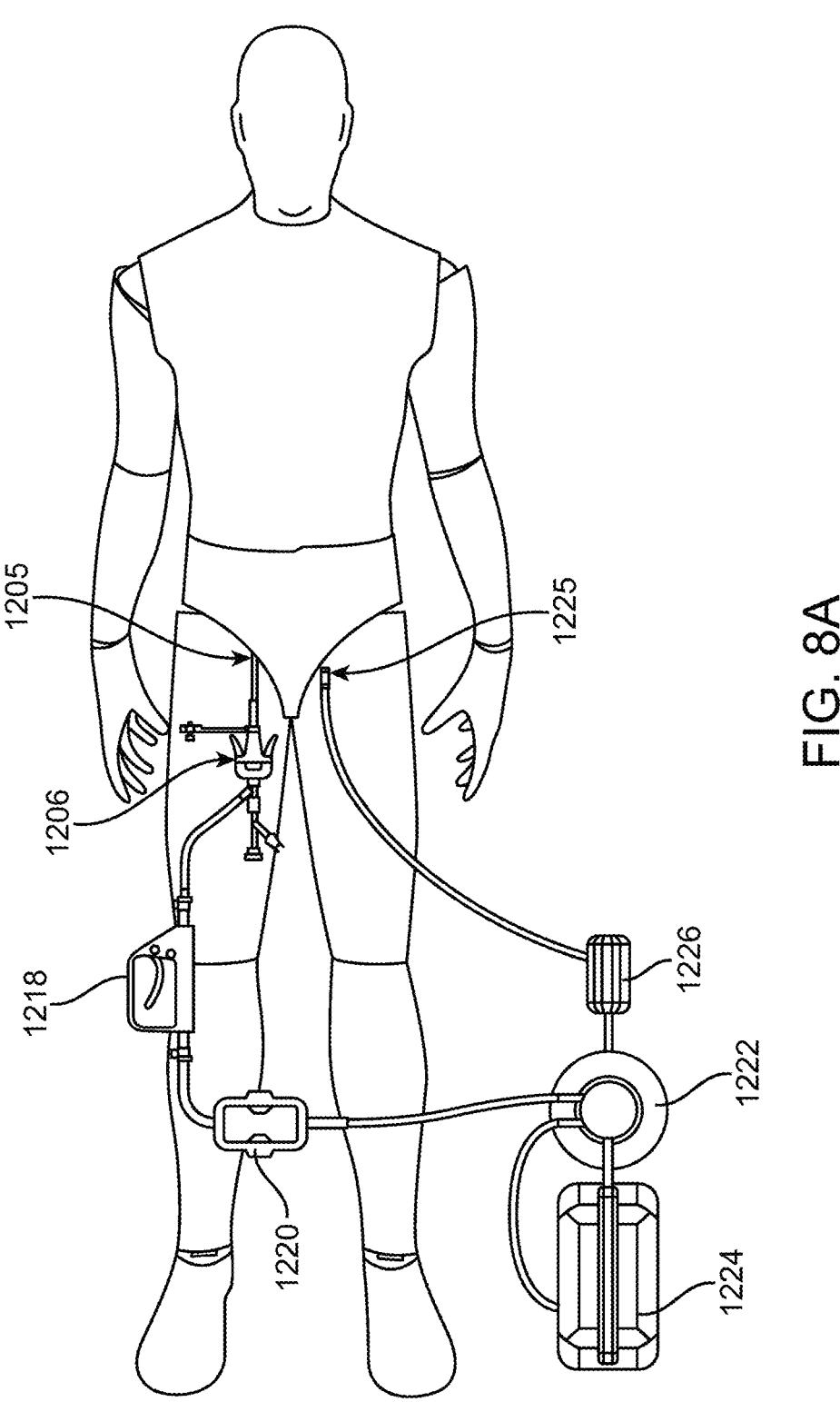
FIGS. 8A-8B illustrate an example of a system including a rigidizing aspiration sheath catheter configured with a blood return circuit including a blood bag, as described herein.
Figure 8B:
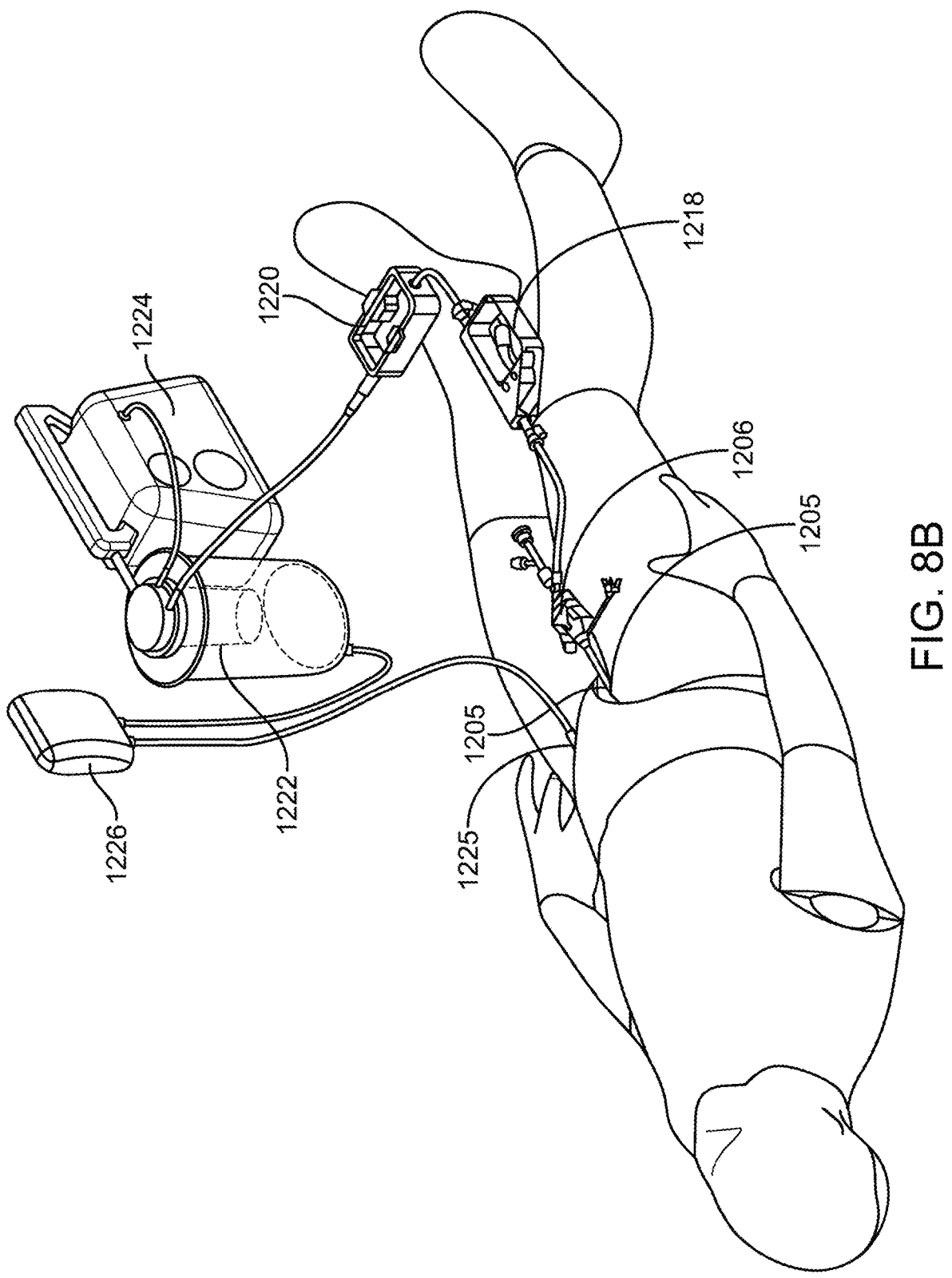

The hemostatic seal region in this example includes a pair of actuators 1042 (shown as levers). Depressing levers 1042 can allow for release of a device (e.g., aspiration catheter) positioned within the rigidizing catheter 1030. When the levers are in their unbiased state, extending outwardly from the body of the seal 1032, the seal valve is closed (shown in FIG. 7D, below).

In FIG. 1F a bladder adapter 1044 for connecting the bladder of the rigidizing aspiration sheath catheter 1030 to the seal 1032 is located a distal end of the seal 1032. This connection allows the seal 1032 to maintain pressurization (e.g., insufflation) of the rigidizing aspiration sheath catheter 1030. Distal to the bladder adapter is an adapter 1046 for connection to an outer layer 1048 of the rigidizing aspiration sheath catheter 1030. A shroud 1060 is located distal to the outer layer adapter 1046, for covering the adapters 1044, 1046 and from which the rigidizing catheter 1030 distally extends.

FIG. 1F further shows an example of the layers of the rigidizing aspiration sheath catheter 1030, including the inner layer 1050, the bladder layer 1052, the rigidizing layer 1054 (e.g., in some examples the rigidizing layer comprises a plurality of filaments that cross over each other, such as, but not limited to, a braid layer, knit layer, woven layer, etc.), and the outer layer 1048. At the distal end of the rigidizing aspiration sheath catheter 1030 is a distal tip 1058.

FIG. 1G shows an end view of the rigidizing catheter shown in FIGS. 1D-1F, in which the rigidizing aspiration sheath catheter includes an atraumatic, distal tip.

In some embodiments, the rigidizing aspiration sheath catheter inner lumen comprises a hydrophilic coating. This coating can help facilitate insertion of an obturator and other devices and accessories.

In some embodiments, an outer surface of the rigidizing aspiration sheath catheter comprises a hydrophobic coating. This type of coating can help facilitate smooth motion through an introducer sheath.

The rigidizing aspiration sheath catheter 1030 may have an inner lumen diameter of the lumen of about 0.03-0.6 in. In some embodiments, the rigidizing aspiration sheath catheter 1030 inner lumen diameter is about 0.16 in. This inner diameter allows compatibility with a 12F catheter. In some embodiments, the inner lumen diameter is about 0.2-0.3 in. This inner diameter allows compatibility with a 20F catheter. In some embodiments, the rigidizing catheter inner lumen is about 0.34 in. This inner diameter allows compatibility with a 26F catheter.

In some embodiments, the rigidizing catheter outer diameter is about 0.2-0.4 in. In some embodiments, the outer diameter is about 0.23 in. or about 18F. In some embodiments, the outer diameter is about 0.34 in. or about 26F. In some embodiments, the rigidizing catheter as a length of about 70-120 cm (or about 80-115 cm, or about 85-115 cm, etc.). In some embodiments, the rigidizing catheter has a minimum bend radius of about 1-2 in. (or about 1.5 in.).

The system can include an obturator 1084 which can be used during navigation of the rigidizing aspiration sheath catheter 1030. Examples of obturators 1084 are described in International Application No. PCT/US2023/062206, filed Feb. 6, 2023, the entirety of which is incorporated by reference herein. The obturator 1084 can comprise a connector 1062 at its proximal end. The obturator 1084 may be configured to be inserted into the rigidizing aspiration sheath catheter 1030 through the hemostatic seal. Once the obturator 1084 is completely inserted within the rigidizing aspiration sheath catheter 1030, the obturator 1084 can be rotated to lock it in place with respect to the hemostatic seal. The rotation of connector 1062 relative to a threaded connection 1064 on the hemostatic seal region may create a lock between the mating mechanism 1064 and corresponding mating mechanism 1066 (e.g., thread, bayonet connection, etc.) on the obturator connector 1062. In some embodiments, the connector 1062 and obturator 1084 are rotated about 90° relative to one another. Other amounts of relative rotation (e.g., about 30-360° are also contemplated).

Figure 2A:
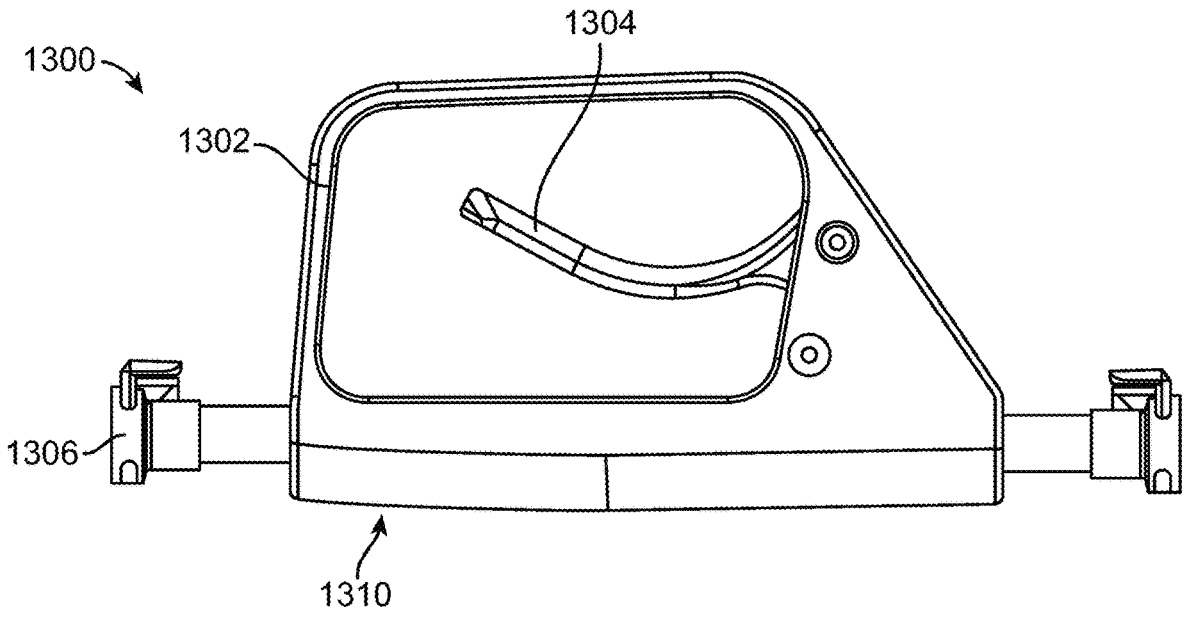
FIG. 2A shows an example of a rigidizing device.
Figure 2B:
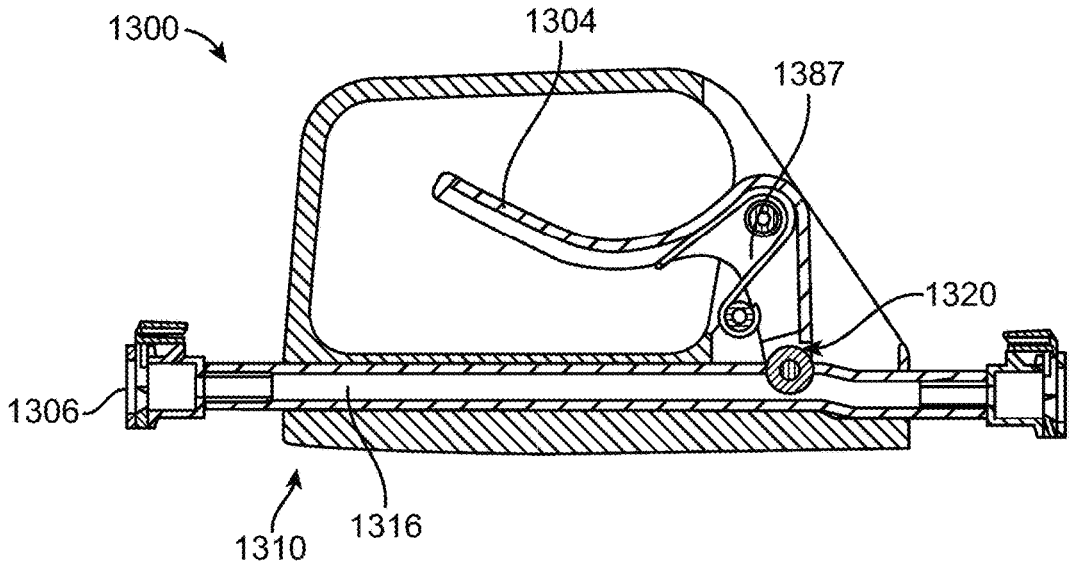
FIGS. 2B-2E show exemplary rigidized shapes of a rigidizing device.
Figure 2C:
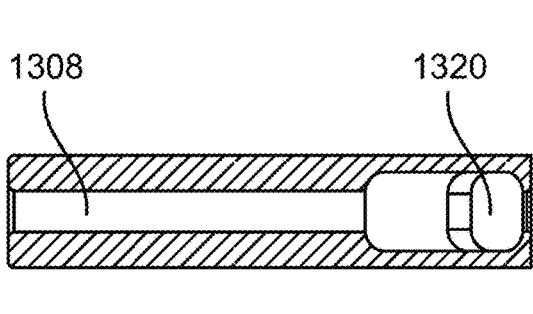
Figure 2D:
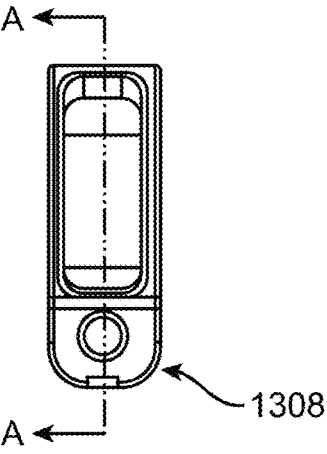

Also described herein are hand-triggered vacuum activation valves. FIGS. 2A-2E illustrate example views of an embodiment of a vacuum activation valve 1300. The hand-triggered vacuum activation valve 1300 includes a handle region 1302 and actuating lever 1304. FIG. 2A shows a side view of the vacuum activation valve 1300. FIG. 2B shows a side sectional view. FIG. 2C shows a sectional view taken through the base region of the handle shown in FIGS. 2A and 2B. A front view is shown in FIG. 2D.

The hand-triggered valve 1300 includes a lower portion 1310 through which the vacuum line 1316 extends. A groove or channel 1308 configured to receive that vacuum line is shown in the section view of FIG. 2C. A clamp 1320 is positioned over the channel 1316. The clamp 1310 is configured to clamp down on the vacuum line when the lever 1304 is actuated. In some examples, the clamp 1320 is configured to unclamp the vacuum line when the lever 1304 is actuated. In the un-actuated state the clamp may be configured to pinch down on (and close off) the vacuum line.

Positioned above the lower portion is a handle 1302 comprising a loop extending distally from a proximal portion of the handle. The loop can be sized to be able to be gripped within the palm of a user. The lever 1304 extends proximally from a proximal portion of the hand-operated valve 1300. The lever 1304 is sized such that it can be actuated by one or more fingers of a user while the handle 1302 is being gripped within the palm of the user. A distance between the handle 1302 and the lever 1304 is selected to enable the lever 1304 to be actuated when the user is gripping the handle 1302. In some embodiments, the distance is about 0.3-1.5 inches. The loop (as shown in the side view) may comprise a number of shapes (polygonal, rectangular, ovular, etc.).

In FIGS. 2A-2D the lever 1304 is shown in an unactuated state, so that the clamp pinches the channel 1316 shut. In some examples the lever and/or the clamp may be biased in the closed state by a bias 1387 (shown as a spring bias). When the lever is actuated, e.g., by pushing it down, the clamp 1320 may be pulled open, away from the channel 1316, allowing suction to pass.

Figure 2E:
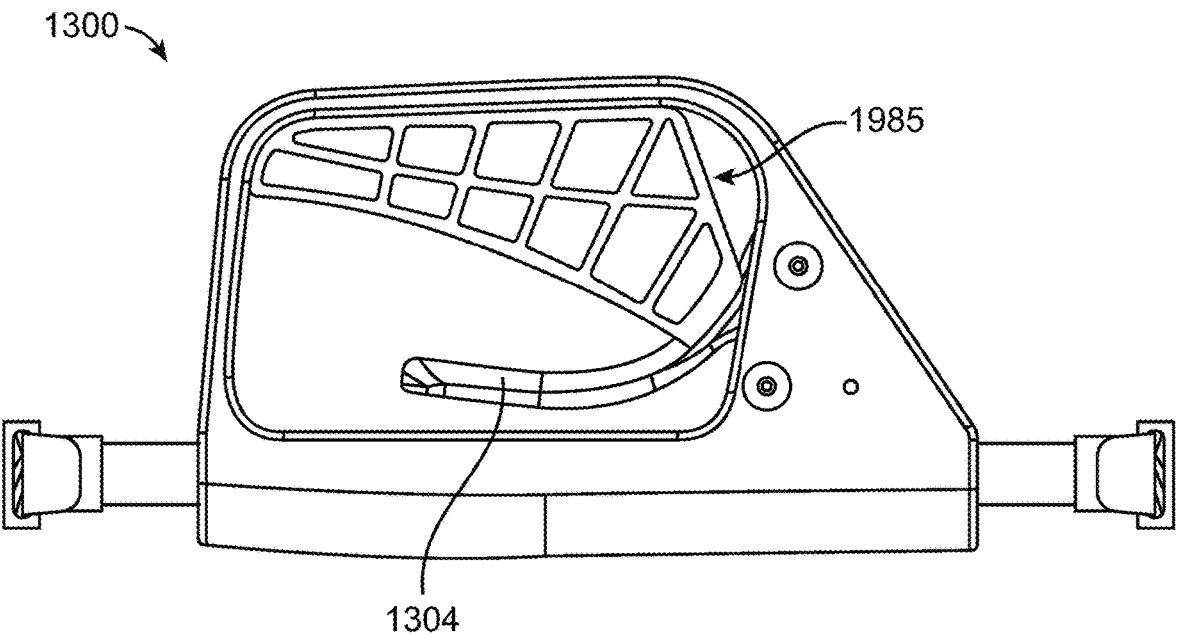

In some cases it may be helpful to store a vacuum activation valve 1300 with the control (e.g., lever 1304) in a closed/actuated position. This may prevent deformation of the valve (e.g., clamp, crip, etc.) mechanism and/or the channel 1316. For example, FIG. 2E shows an example of a vacuum activation valve 1300 in which a retainer 1395 is coupled thereto, to hold the lever 1304 in a closed position, maintaining the channel within the vacuum activation valve in an open position. The retainer may be removed before use, e.g., once connected to the fluid line.

The valve can have any appropriate length. In some examples the valve has a length of about 4-6 in (or about 3-5, 5-7, 5-6 in., etc.). The handle may be any appropriate length. For example, the length of the handle can be about 3-5 in. (or about 2-4 in., 4-6 in. 4-5 in., etc.). The length of the lever can be, e.g., about 3-5 in. (or about 2-4 in., 4-6 in. 4-5 in., etc.). The lever can be curved as shown in FIG. 2A. In other embodiments, it is straight or angular.

Figure 3A:
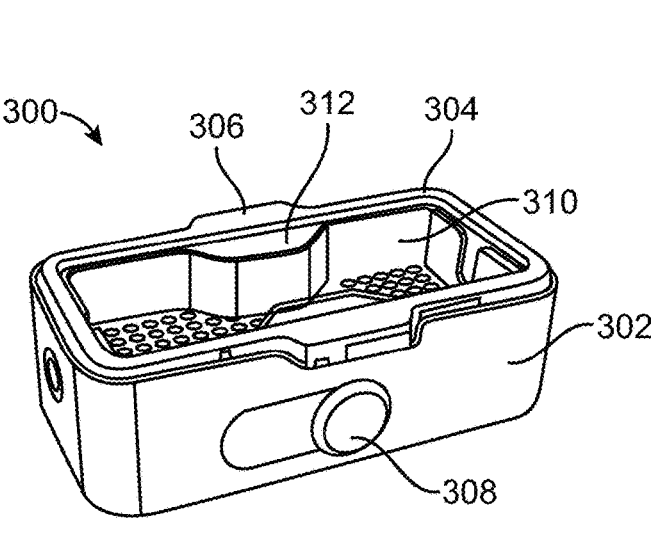
FIGS. 3A-3H show various views of a clot capture chamber.

Also described herein are clot capture chambers (also referred to as clot capture containers). The clot capture chambers may be configured to capture and clot material from the patient's blood. FIGS. 3A-3D show views of an example of an embodiment of a clot capture chamber (e.g., like that shown in FIG. 1B). FIG. 3A is a perspective view of a clot capture chamber. The clot capture component 300 comprises a container 302 with a lid 304. The lid 304 can be completely removed from the container 302. In some embodiments, the lid is connected to the container by a hinge. The lid 304 can comprise one or more tabs 306 extending or projecting from an edge of the lid to aid in lifting and/or removal of the lid. In some embodiments, the lid is transparent, which can advantageously allow for visualization of aspirated material therethrough.

When under negative pressure from an attached vacuum source, the lid may be sealed to the container. To enable removal of the lid, a user may perform a vent to atmosphere to release the negative of pressure within the container. In some embodiments, this venting is controlled by a button 308 positioned on the container.

The container 302 can have a generally rectangular prism shape. Other shapes are also possible (e.g., square prism, elliptic cylinder, etc.). In some embodiments, the container 304 comprises a length of about 3-5 in. (or about 2.5-5.5 in., 3.5-4.5 in., about 4 in., etc.). The container can have a width of about 1-3 in. (or about 0.75-3.25 in., 1.5-2.5 in., about 2 in., etc.). The container can have a depth of about 0.3-1.1 in. (or about-4-1.0 in., 0.5-0.9 in., 0.6-0.7 in., etc.).

Figure 3B:
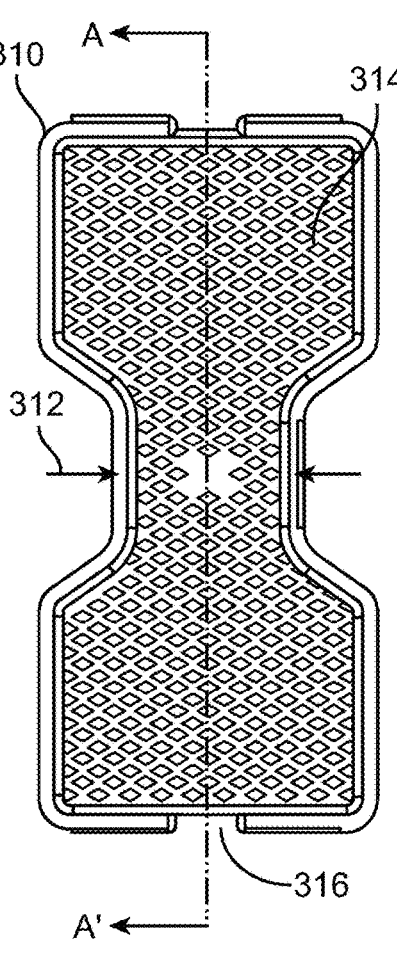
Figure 3C:
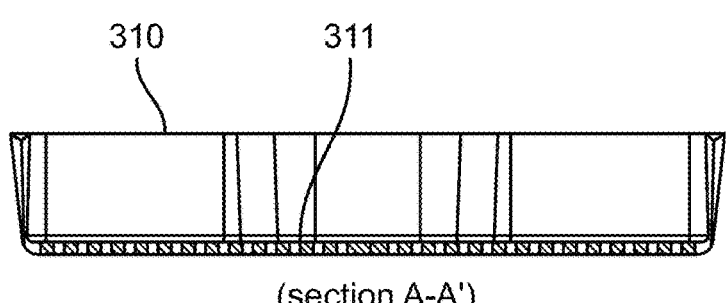
Figure 3D:
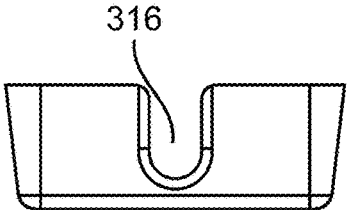

Positioned within the container is a tray 310. FIG. 3B shows a top view of the tray 310. FIG. 3C shows a section view taking along line A-A of FIG. 3B. FIG. 3D shows a front view of the tray 310. In some embodiments, the tray 310 is removable from the container 302. The tray 310 is sized to conform to an inner perimeter of the container 302. The tray 310 may have one or more regions 312 where it is spaced away from an inner perimeter of the container 302 to enable easy removal of the tray 310 from the container.

The tray 310 includes one or more intermediate surface(s) 311 having apertures 314 to allow for draining of blood and other fluids. In some embodiments, the intermediate surface comprises a screen or mesh like configuration. The apertures may be any sized to permit fluid (e.g., blood) to flow through, but retain clot material. The apertures (e.g., mesh) may be any appropriate size. For example, the apertures may be between about 0.037 mm and about 6 mm (e.g., between about 0.05 mm and about 5 mm, between about 0.1 mm and about 4 mm, between about 0.2 mm and 3 mm, between about 0.3 mm and 2.5 mm, between about 0.5 mm and about 4 mm, between about 0.75 mm and about 4 mm, etc.). In some examples the intermediate surface may include multiple layers of mesh having different mesh sizes in order to progressively filter out smaller and smaller clot sizes without clogging the chamber. The different layers may be separated by a gap (e.g., of between about 0.5 mm to 2 cm). These mesh regions may be removable to allow analysis and/or capture of the different size clots and/or cleaning (including sterilization).

The tray 310 may include channels 316 along two opposing sides to allow access to a vacuum lumen. The channels 316 may be U-shaped. This shape may allow the channels to partially surround a vacuum aperture on a side of the container.

The tray can have a length of about 3-5 in. (or about 2.5-5.5 in., 3.5-4.5 in., about 4 in., etc.). The tray can have a width of about 1-3 in. (or about 0.75-3.25 in., 1.5-2.5 in., about 2 in., etc.). The tray can have a depth of about 0.3-1.1 in. (or about-. 4-1.0 in., 0.5-0.9 in., 0.6-0.7 in., etc.).

In some embodiments, the tray comprises a polymer, such as acrylonitrile butadiene styrene (ABS).

Figures 3E, 3F:
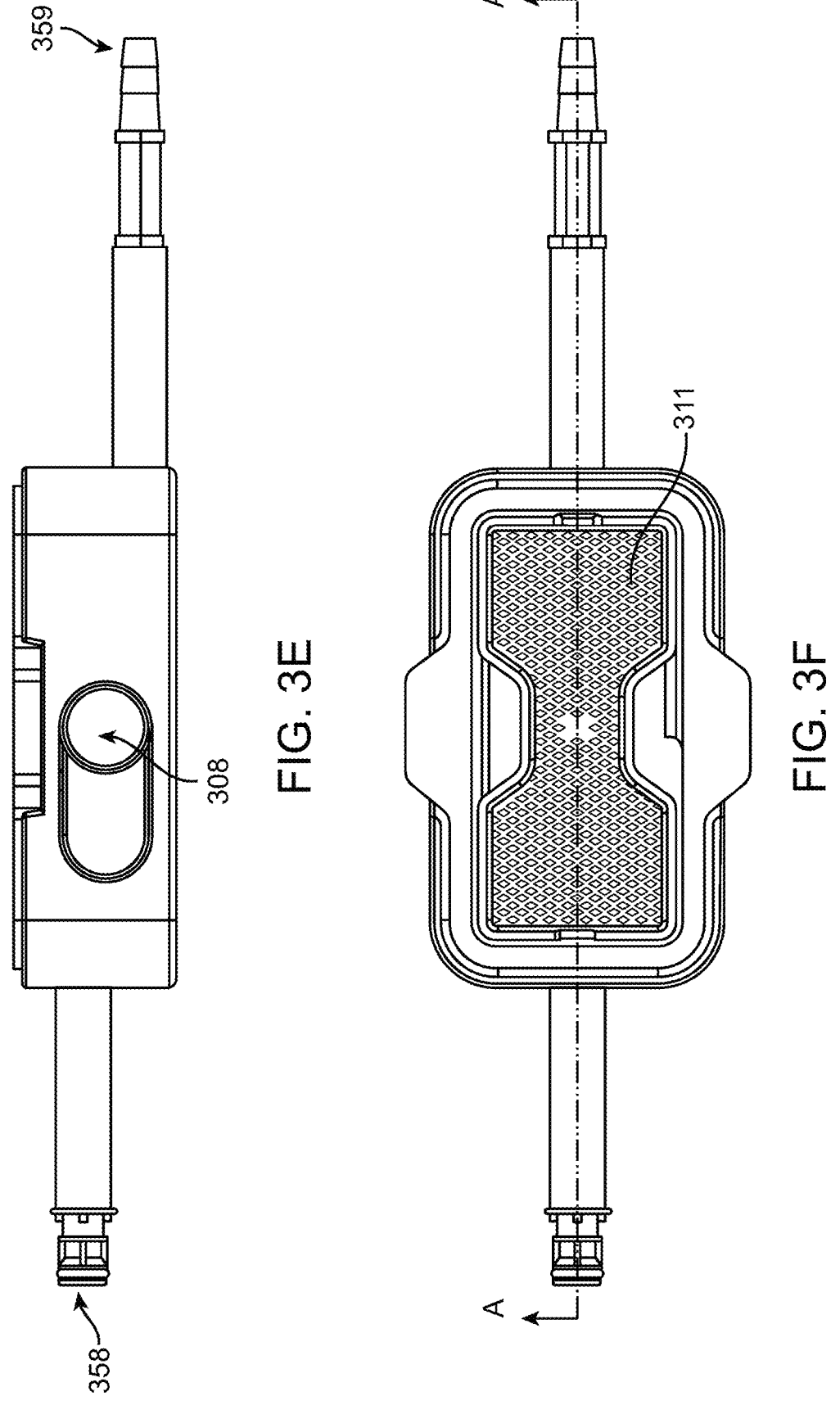
Figures 3G, 3H:
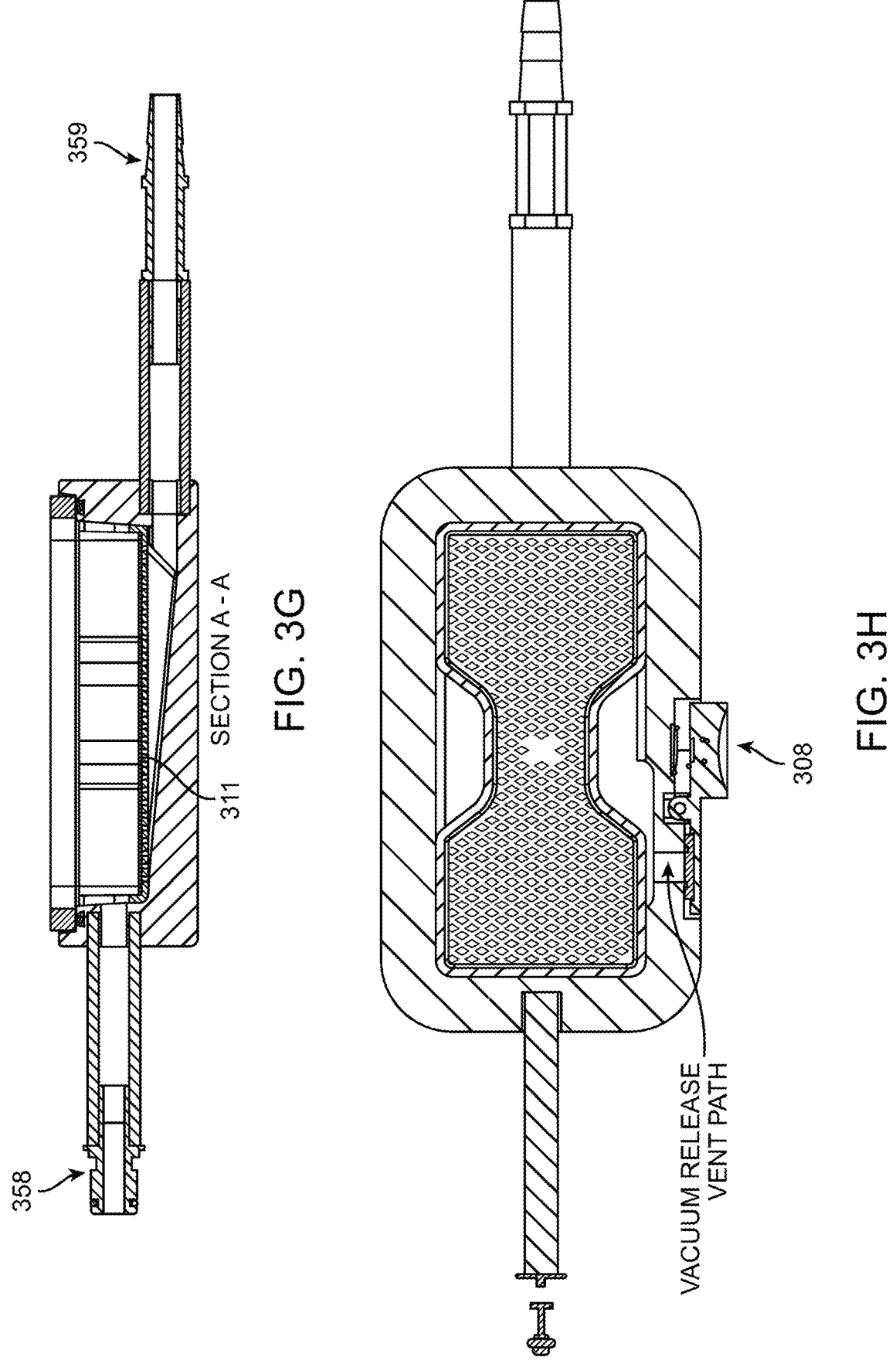

FIGS. 3E-3H show side, top, side section and top section views, respectively of an example of a clot capture chamber as described herein. In FIG. 3E a vacuum release valve 308 is positioned on the side of the chamber the device may be connected in-line as part of the vacuum line, so that fluid is drawn in from the top inlet line 358, so that the fluid (e.g., blood with clot material) enters the upper region of the chamber and into the tray; the blood may then drain to the bottom of the chamber and out of the outlet 359, as shown in the sectional view of FIG. 3G. In any of these clot capture chambers the inlet may be positioned at a top region, and the outlet may be positioned at the bottom region, allowing gravity to assist in passing the blood through the porous intermediate layer(s). Any of these apparatuses may include a seal (e.g., gasket) between the main body and the lid, as shown in section view of FIG. 3G.

An exemplary method of using the aspiration system described herein comprises navigating through the vasculature to or near a desired clot treatment site using a guidewire (e.g., 0.014" or a 0.035" wire). A rigidizing catheter can then be advanced, in a flexible state, over the guidewire to or near the clot treatment site. Once at or near the site, the rigidizing catheter may be transitioned to the rigid state. An obturator can be used during advancement of the rigidizing catheter. At this point, the guidewire may be removed, if so desired. Removing the guidewire can advantageously free up space within the lumen of the rigidizing catheter.

Once the rigidizing catheter is in the rigid space, it creates a stable conduit or platform from which treatment can be initiated. An aspiration catheter can be advanced through the rigidizing catheter. The aspiration catheter can have a proximal connector configured to lock to the hemostasis valve of the rigidizing catheter. The aspiration catheter can have a bigger inner lumen than traditional aspiration catheters because the stable platform created by the rigidizing catheter reduces the need for the aspiration catheter to perform accurate navigation and allows it to have a larger central bore. As mentioned here, the rigidizing catheters described herein may provide sufficient support (e.g., mechanical integrity) to one or more additional devices or components to allow these additional components (guidewires, aspiration catheter, stent, heart valve, tools, etc.) to be more flexible than other components. The stiffness necessary for the control and operation of a standalone component may become redundant when used within the rigidizing catheters described herein, which may provide the mechanical support that is otherwise required in the standalone component.

In some embodiments, the aspiration catheter can be switched out for a different aspiration catheter (e.g., comprising a different size). The hemostasis valve can be actuated to release the first aspiration catheter and insert the second aspiration, allowing for a quick exchange of the aspiration catheters. The aspiration catheter handle can be actuated to release the first aspiration catheter from the vacuum line and a second aspiration catheter can be connected to the vacuum line.

In some embodiments, the aspiration catheter may be removed to allow for flushing of the aspiration line. The rigidization catheter maintaining the stable pathway to the treatment site allows for this flushing to occur without losing the catheter position.

In some embodiments, the method further comprises visualizing aspirated material through the transparent lid of the clot capture container. In some embodiments, the container may be vented, and the lid removed. The tray may be replaced with another clean tray, for example, if the container is getting full. Traditional aspiration systems do not allow for a large enough aspiration lumen size to aspirate enough material to require this replaceable tray feature. A single tray can be used throughout the procedure, or multiple trays can be used—for example, one tray for each suction attempt or for each clot removed.

In some embodiments, aspiration can be performed directly through the rigidizing catheter.

Figure 4A:
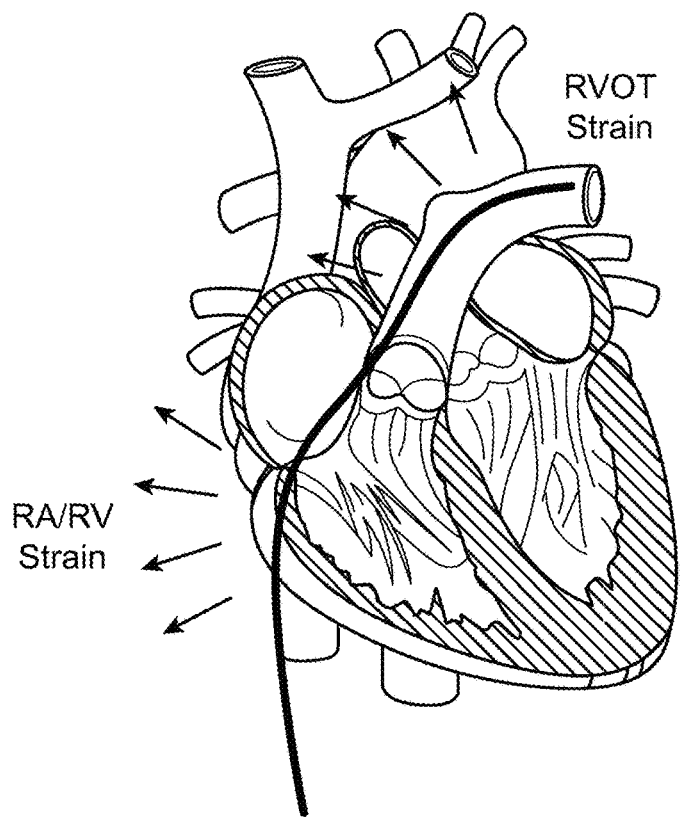
FIGS. 4A and 4B show a traditional catheter and a rigidizing catheter, respectively, navigating to the pulmonary artery.
Figure 4B:
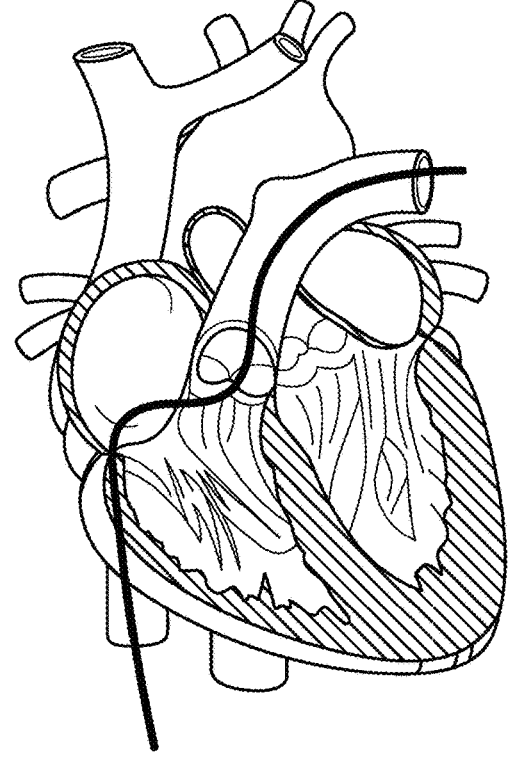

FIGS. 4A and 4B show a traditional catheter navigated to the pulmonary artery (FIG. 4A) and the rigidizing system described herein navigated to the pulmonary artery (FIG. 4B). As shown in FIGS. 4A and 4B, the rigidizing system's ability to establish the pathway in a flexible state leads to reduced strain and reduced potential for hemodynamic compromise and injury.

In general, the removal of clot material may result in the loss of large blood volumes. Blood loss can be associated with the duration of the aspiration and the proximity of the aspiration catheter tip to the clot. However, the methods and apparatuses described herein may be configured to minimize blood loss. For example, the use of rigidizing apparatuses as described herein may allow apparatuses to be positioned proximate to the clot, which may minimize the blood volume required to move the clot. The stabilization achieved with the rigidizing catheters described herein may improve access to the clot and lead to better engagement between the tip of the aspiration catheter and the clot, resulting in lower blood loss by virtue of early and improved clot engagement. In addition, the methods and apparatuses described herein may be used without the use of guidewires. In particular, the apparatuses described herein may be configured to accommodate a cardiotomy reservoir (e.g., a suction canister/blood filter), which may be integrated within a thrombectomy circuit as described herein.

Figure 5A:
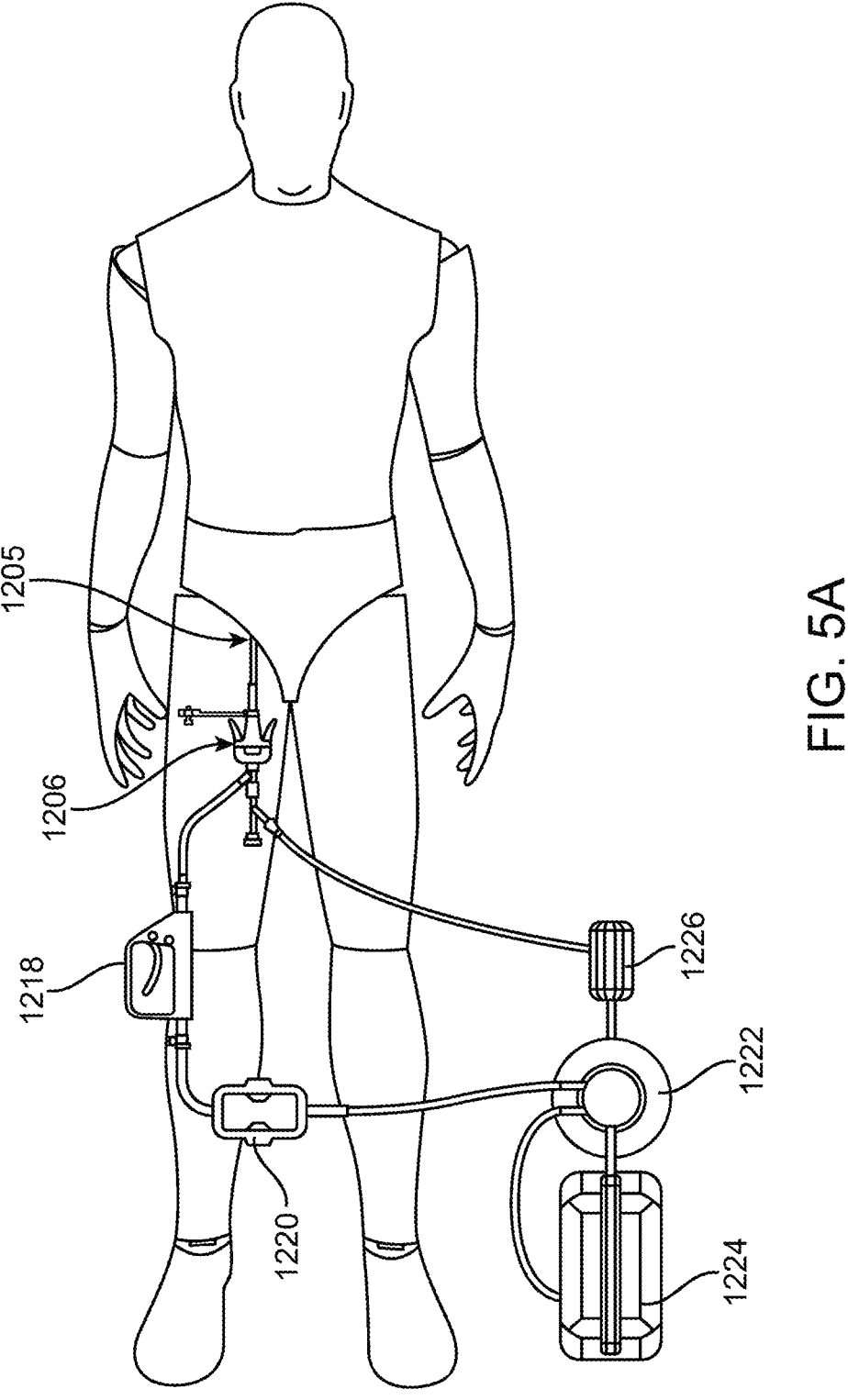
FIGS. 5A-5B illustrate an example of a system including a rigidizing aspiration sheath catheter configured with a blood return circuit, including a blood filter and blood bag as described herein.
Figure 5B:
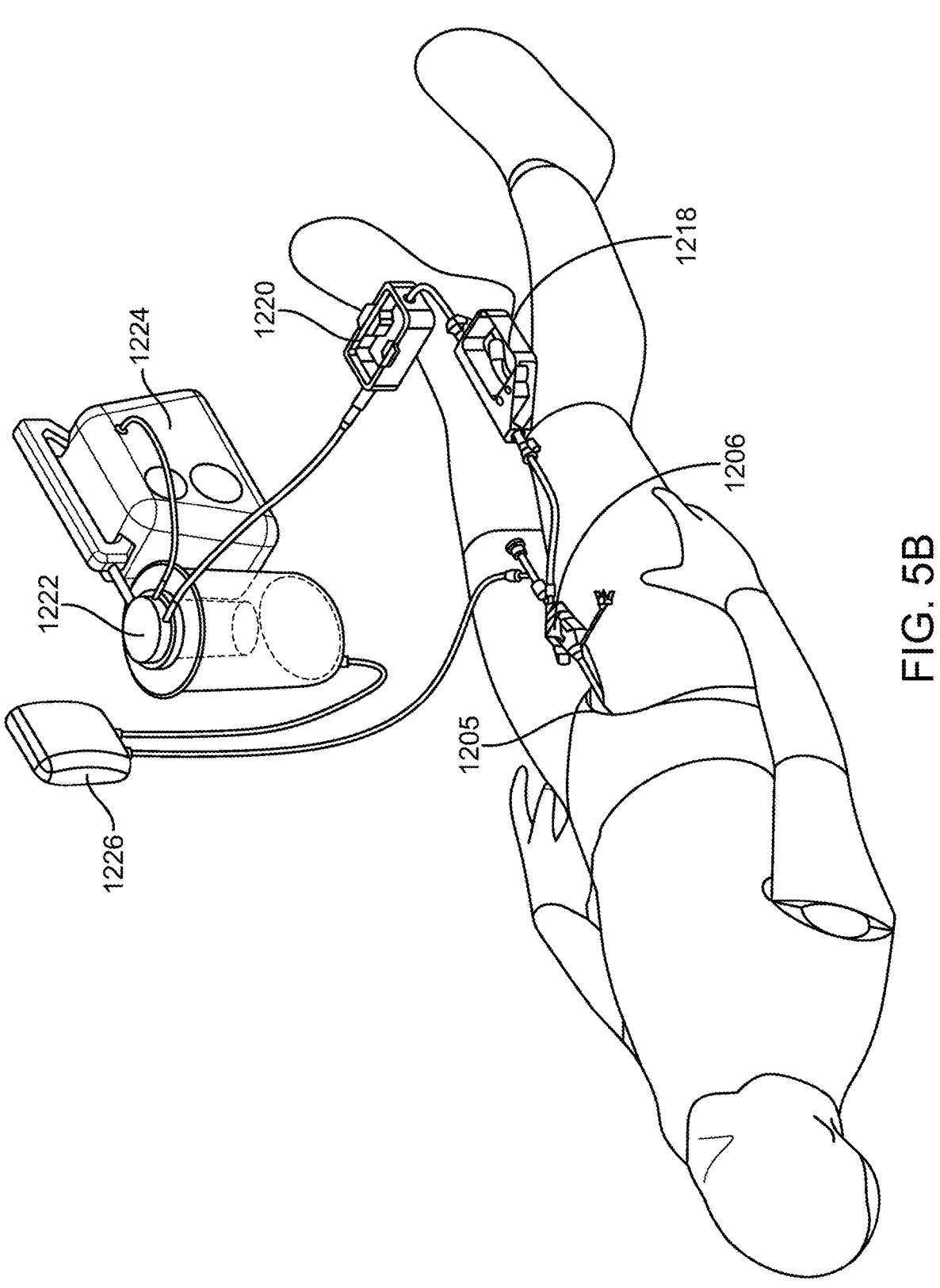

FIGS. 5A-5B, 6A-6B, 7A-7B, 8A-8B and 9A-9B illustrate examples of systems including a rigidizing aspiration sheath catheter configured with a blood return circuit. In general, these apparatuses may be configured for use with a patient to remove, aspirate material, and in particular clot material, from the vascular system of a patient. In any of these examples the apparatus may include a return circuit for returning and/or replacing blood removed during the procedure. For example, FIG. 5A illustrate a system as described herein including any of the rigidizing aspiration catheters 1206 described herein. The aspiration catheter may be coupled to a hand-operated valve (extraction handle 1218) that connects the aspiration tube in-line with the clot capture container 1220, which is in turn connected in-line with a suction canister including one or more blood filters 1222. The suction cannister may be held under vacuum to a negative pressure set by a vacuum pump 1224.

The suction cannister may filter and/or treat the blood so that it may be reintroduced into the body. For example the suction canister 1222 may include filtration to remove clot material and/or may be treated with one or more agents to reduce or prevent infection and/or to reduce and prevent clotting (e.g., anticoagulants). As mentioned above, the optional clot capture 1220 device may also filter clot material before it reaches the suction canister 1222. In general the filtered and/or treated blood may be reintroduced back into the body either directly or indirectly, e.g., by first passing to a blood bag 1226. Supplemental blood may be provided.

In general, the sterility of the operating sterile field may be maintained by keeping all of these elements (e.g., the blood bag, suction cannister, clot capture device, handle, etc.) within the sterile field. Any or all of these components may be single-use and/or reusable (and sterilizable).

The rigidizing aspiration catheter may be inserted into an access site 1205 on the patient's body, such as the femoral artery. Note that any appropriate access region may be used (e.g., radial, ulnar, axillary, brachial, *dorsalis* pedis, posterior tibial). In FIGS. 5A-5B and 6A-6B the system is configured so that the material, including blood, is removed and returned via the same access site 1205. Alternatively, in some examples the return site may be a separate access site, such as illustrated in FIGS. 7A-7B and 8A-8B. In these examples the blood return site 1225 may be on the contralateral side (e.g., the contralateral femoral artery).

Figure 6A:
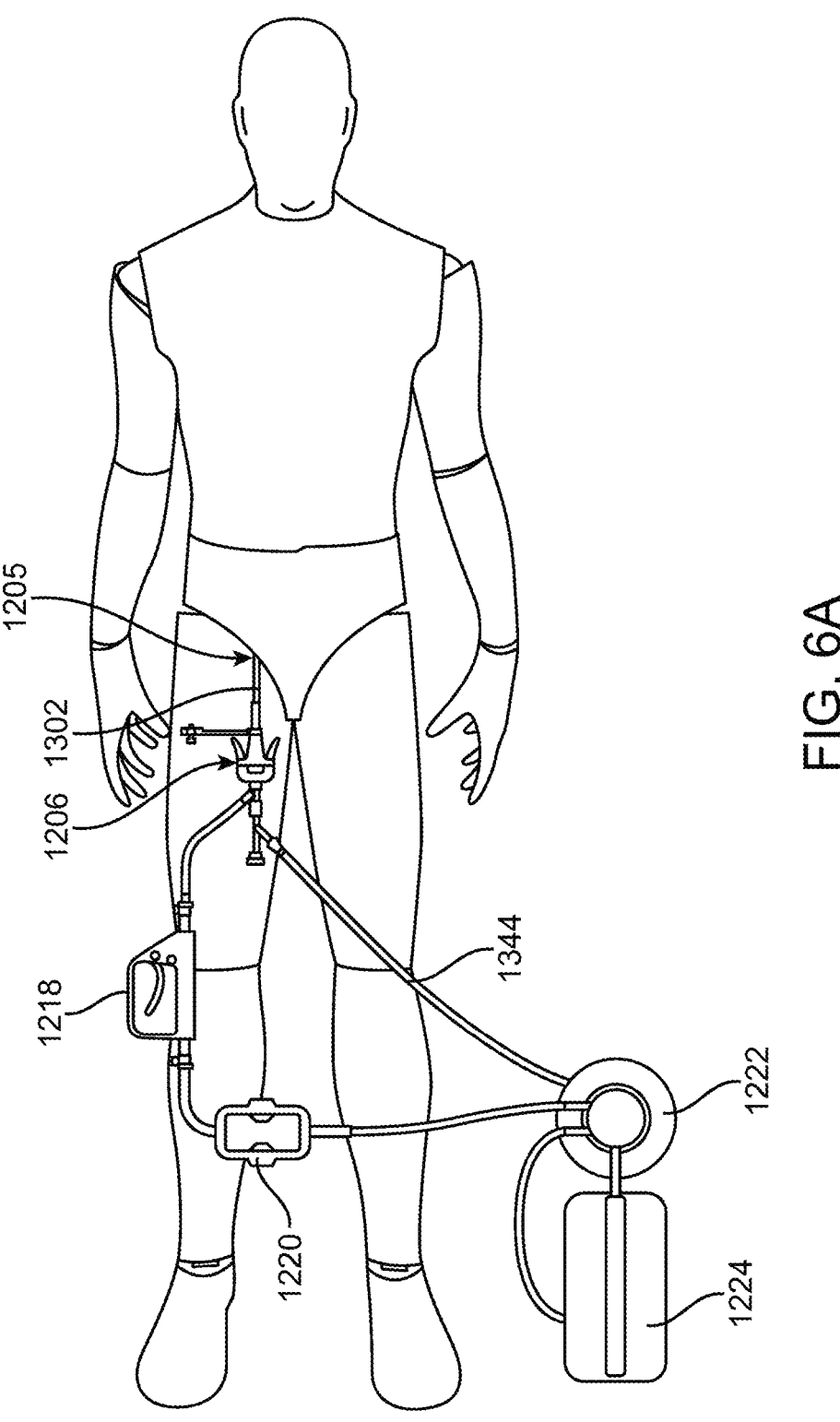
FIGS. 6A-6B illustrate an example of a system including a rigidizing aspiration sheath catheter configured with a blood return circuit without a blood bag, as described herein.
Figure 6B:
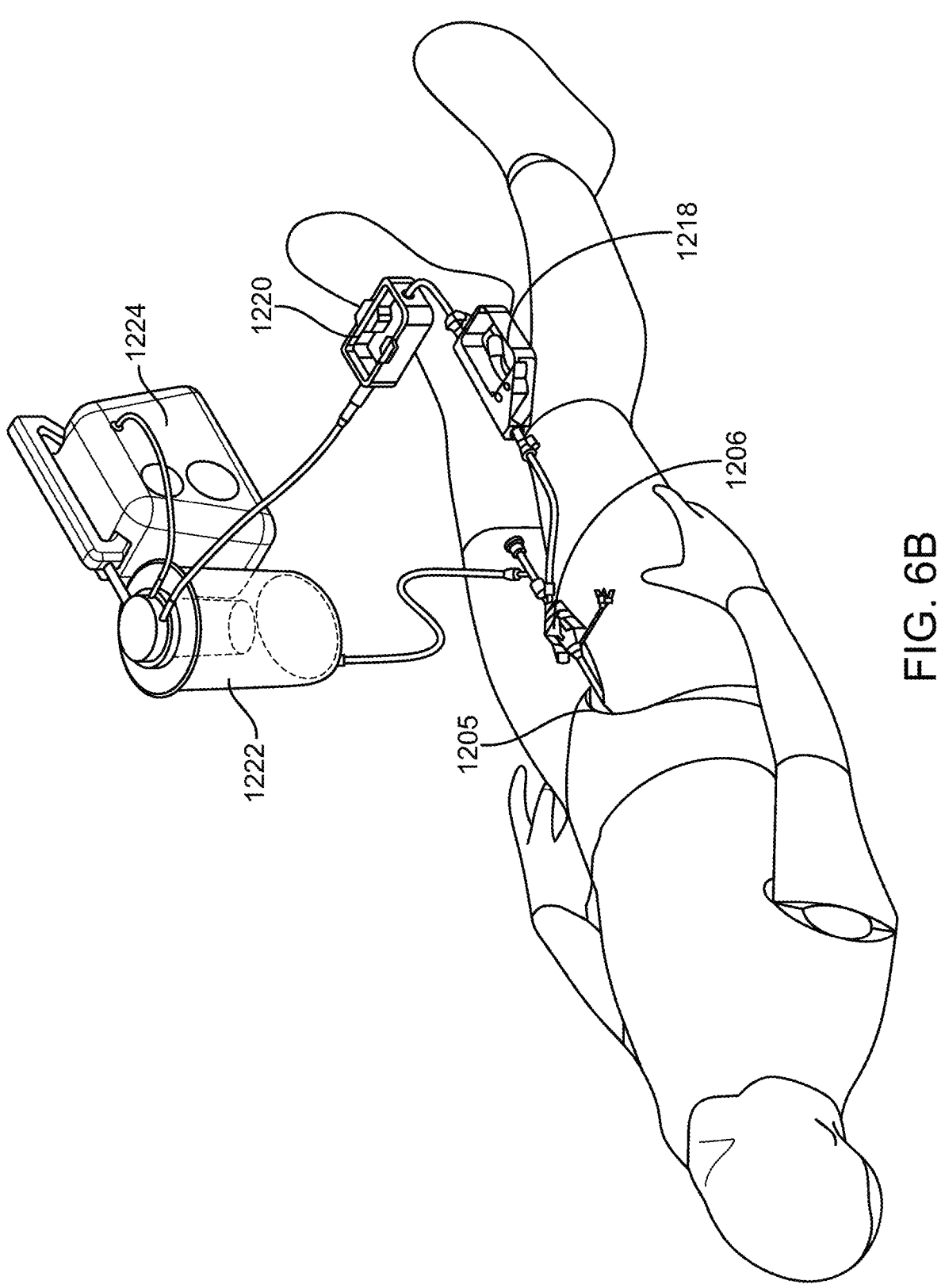

For example, FIGS. 6A-6B illustrate a configuration of an apparatus including a rigidizing aspiration sheath catheter 1302, which includes a hemostasis valve at the proximal end coupled to a suction connector 1206. The suction connector fluidically connects to the control valve (e.g., configured as an actuation handle 1218), in-line with a clot capture chamber 1220 and a blood capture/filter chamber 1222 that is connected to a source of vacuum 1224, similar to FIGS. 5A-5B. In this example, the rigidizing aspiration sheath catheter may be inserted through the access site 1205 and navigated through the body (e.g., over a guidewire) including as shown in FIGS. 4A-4B, across the heart, to a target region to remove clot. Once in position, the rigidizing aspiration sheath catheter may be rigidized, e.g., by applying positive and/or negative pressure, and coupled to the suction line using the connector 1206. Aspiration may be applied, e.g., by actuating the control valve 1218, with the device maintained in the rigid configuration (e.g., by maintaining the positive and/or negative pressure).

In some examples, after aspirating one or more times, by activating and releasing the extraction handle 1218, a state of vacuum may be re-established between extraction handle and the blood capture chamber 1222 (e.g., reservoir), including the portion of the blood return line up to the patient; a check valve may be included on the blood return line. Blood may be held by the blood capture region. In any of these examples, an optional blood return circuit may be included, as shown. In this example, the blood return circuit includes a return tubing line 1344.

In any of these methods, the rigidizing aspiration sheath catheter may be used to support a second catheter, an aspiration catheter, which may be inserted through the rigidizing aspiration sheath catheter, as described above. The rigidizing aspiration sheath catheter may be uncoupled from the suction line, the aspiration catheter inserted through the rigidizing aspiration sheath catheter (e.g., using the posterior hemostasis valve of the rigidizing aspiration sheath catheter) and the aspiration catheter coupled to the suction line, all while the rigidizing aspiration sheath catheter remains in the rigid configuration. Suction may then be applied through the aspiration catheter, while the rigidizing aspiration sheath catheter remains rigid, to support the aspiration catheter.

When it is time to reinfuse blood to the patient the vacuum may be removed (e.g., bringing the system to atmospheric pressure) which may be done by pressing a release control (e.g., button) on the clot capture chamber 1220, which may leak air into the system in a controlled manner. Air and any remaining blood may be in the clot capture chamber 1220 may be driven to the blood capture chamber/filter 1222. In some cases the lid of the clot capture chamber may be taken off to maintain this state. At this point, a user could use a syringe at the check valve to pump/reinfuse blood to the patient, or a more automated blood return may be used.

Figure 9A:
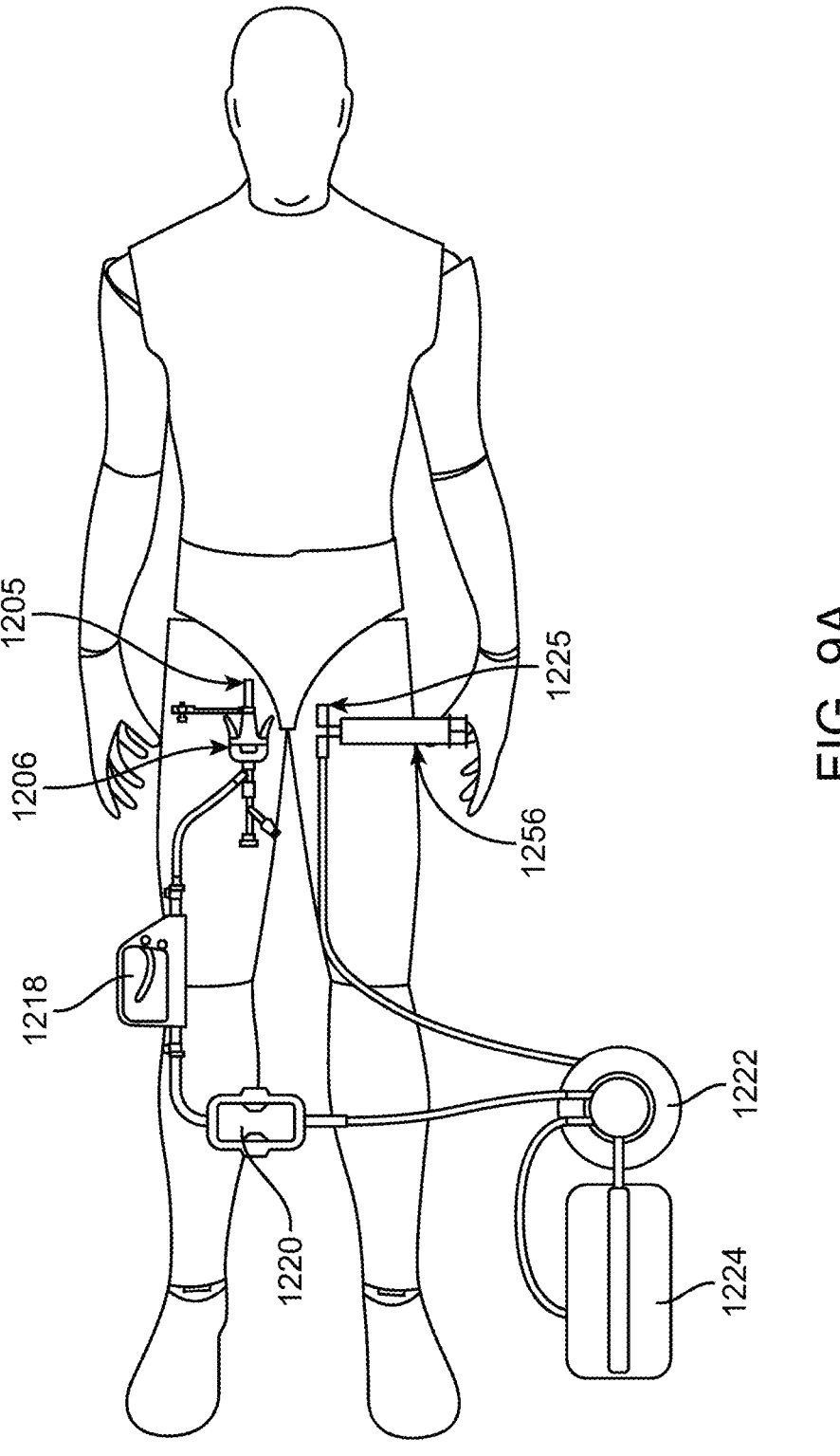
FIGS. 9A-9B illustrate an example of a system including a rigidizing aspiration sheath catheter including a blood return circuit using a syringe, as described herein.
Figure 9B:
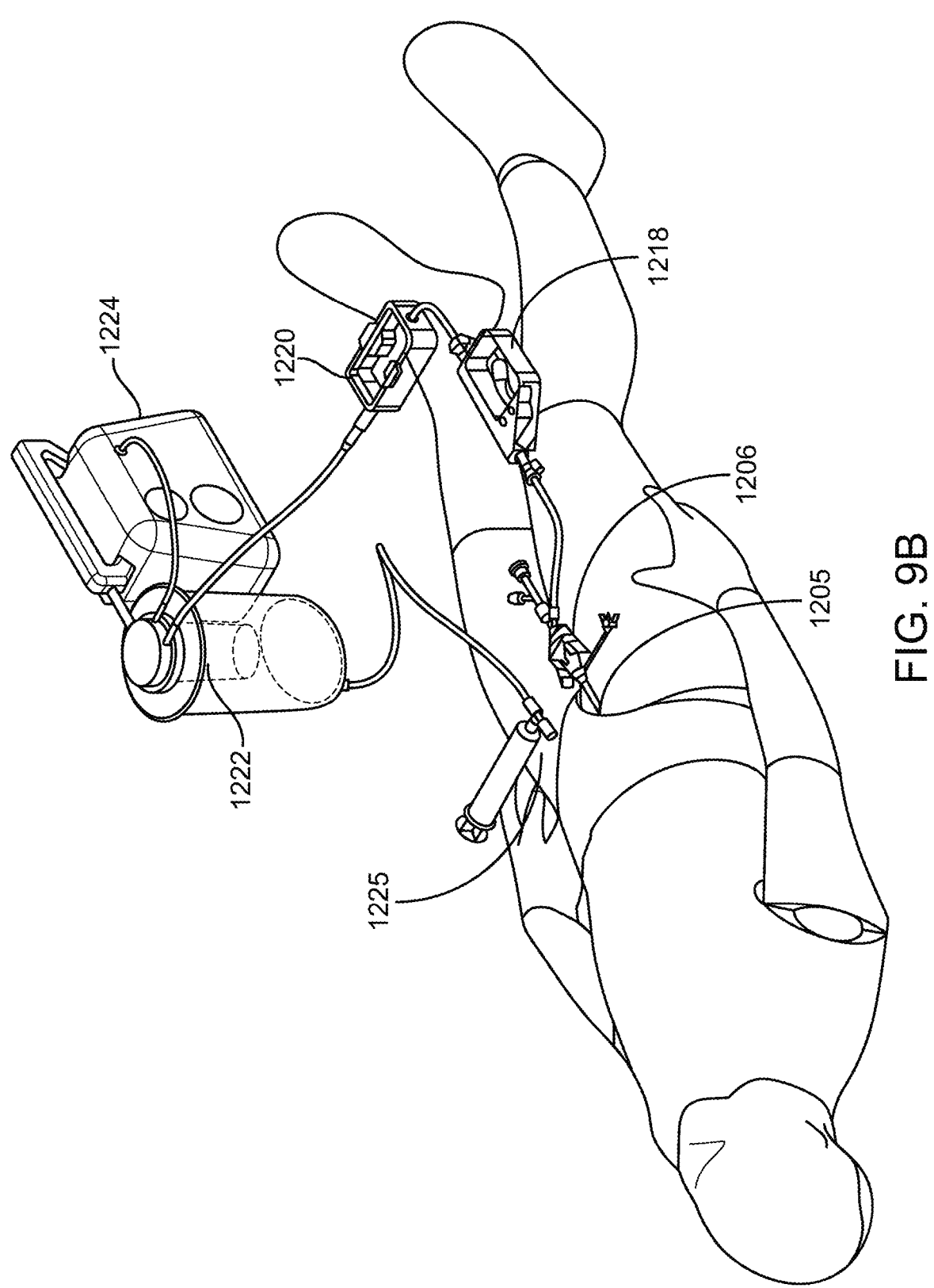
Figure 9C:
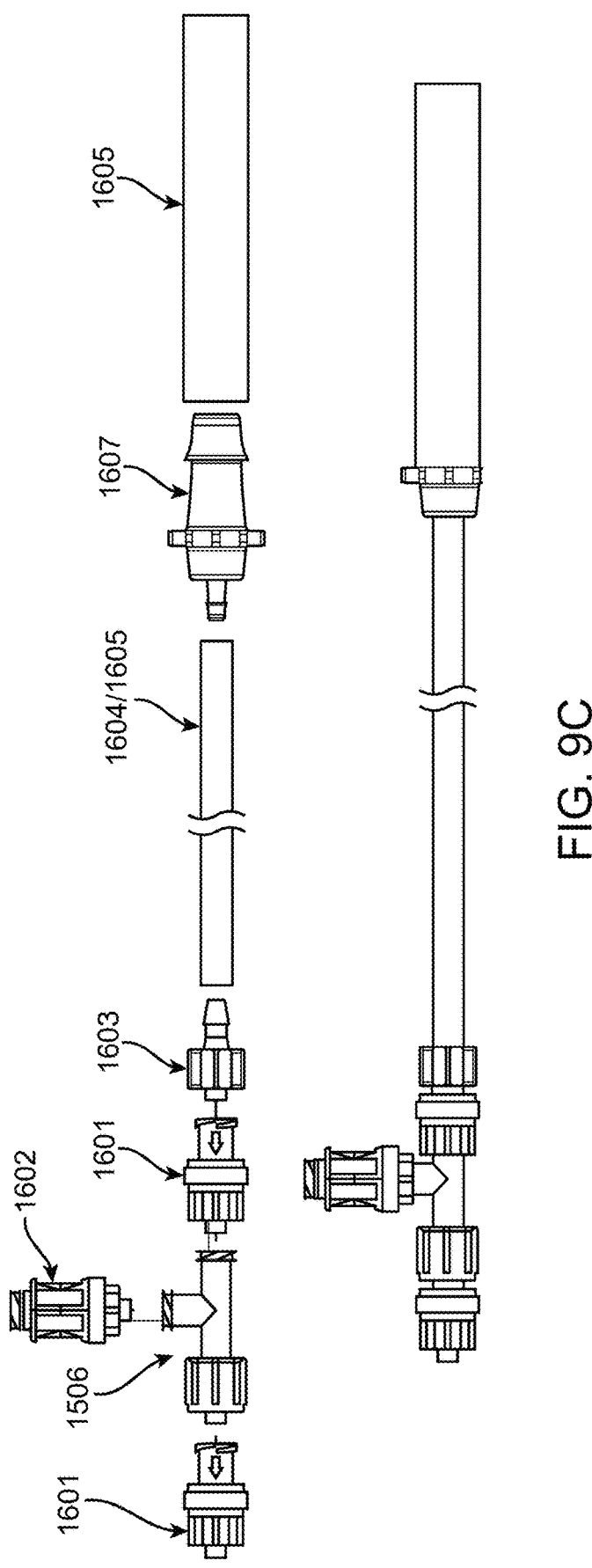
FIG. 9C is an example of a portion of a tubing assembly that may be used with a blood return circuit as described herein.

As mentioned, in some examples the blood return circuit may be direct, and may couple from the suction canister/blood filter directly back into the patient's body, as shown in FIGS. 6A-6B and 6A-6B. For example, blood may exit the patient from the catheter and may be returned to patient through either the catheter (e.g., the rigidizing aspiration sheath catheter or aspiration catheter) or alternate means (not shown). FIGS. 9A-9B illustrate an alternative site 1225 for re-introduction of blood (e.g., on the opposite leg) using a syringe 1256, as mentioned above. FIG. 9C shows an example of a return assembly 1600 including a check valve 1601, a swabble luer fitting 1602, a male luer lock 1603, tubing 1604, 1605, and a T-connector 1506 and a reducer 1607. This blood return tubing assembly may generally include multiple one-way valves arranged so that fluid may be injected into the body while minimizing blood loss.

Figure 10A:
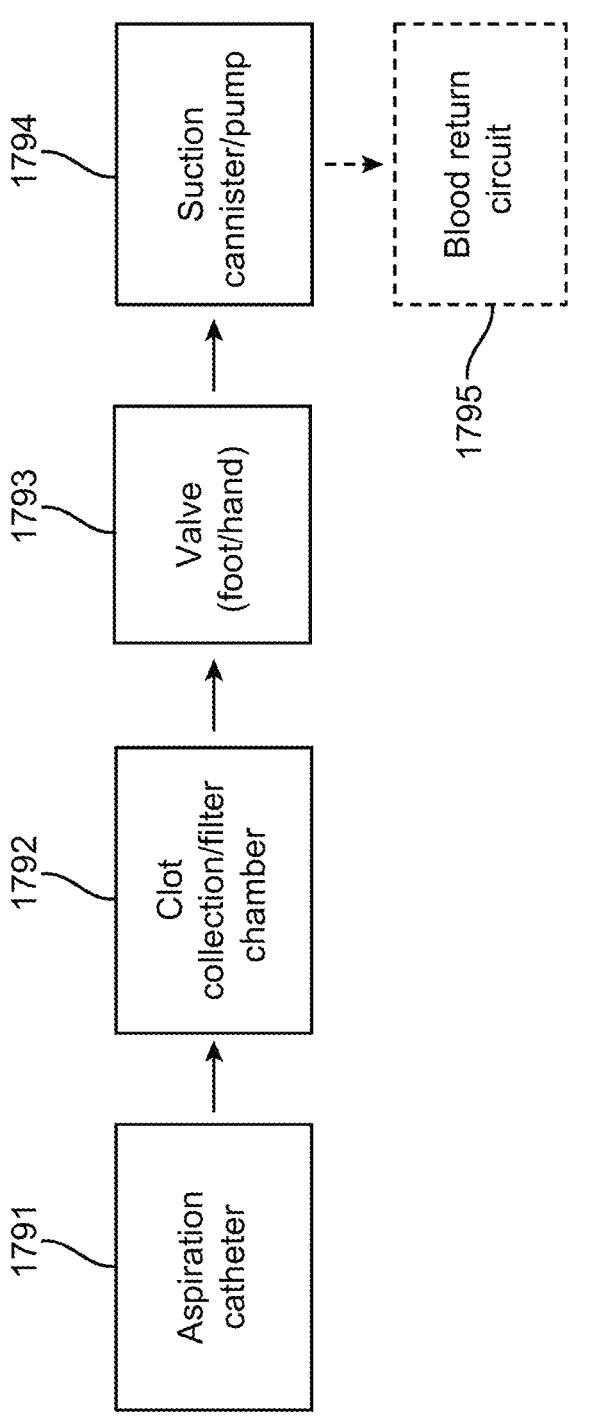
FIGS. 10A-10B illustrate an example of a system including a rigidizing aspiration sheath catheter.
Figure 10B:
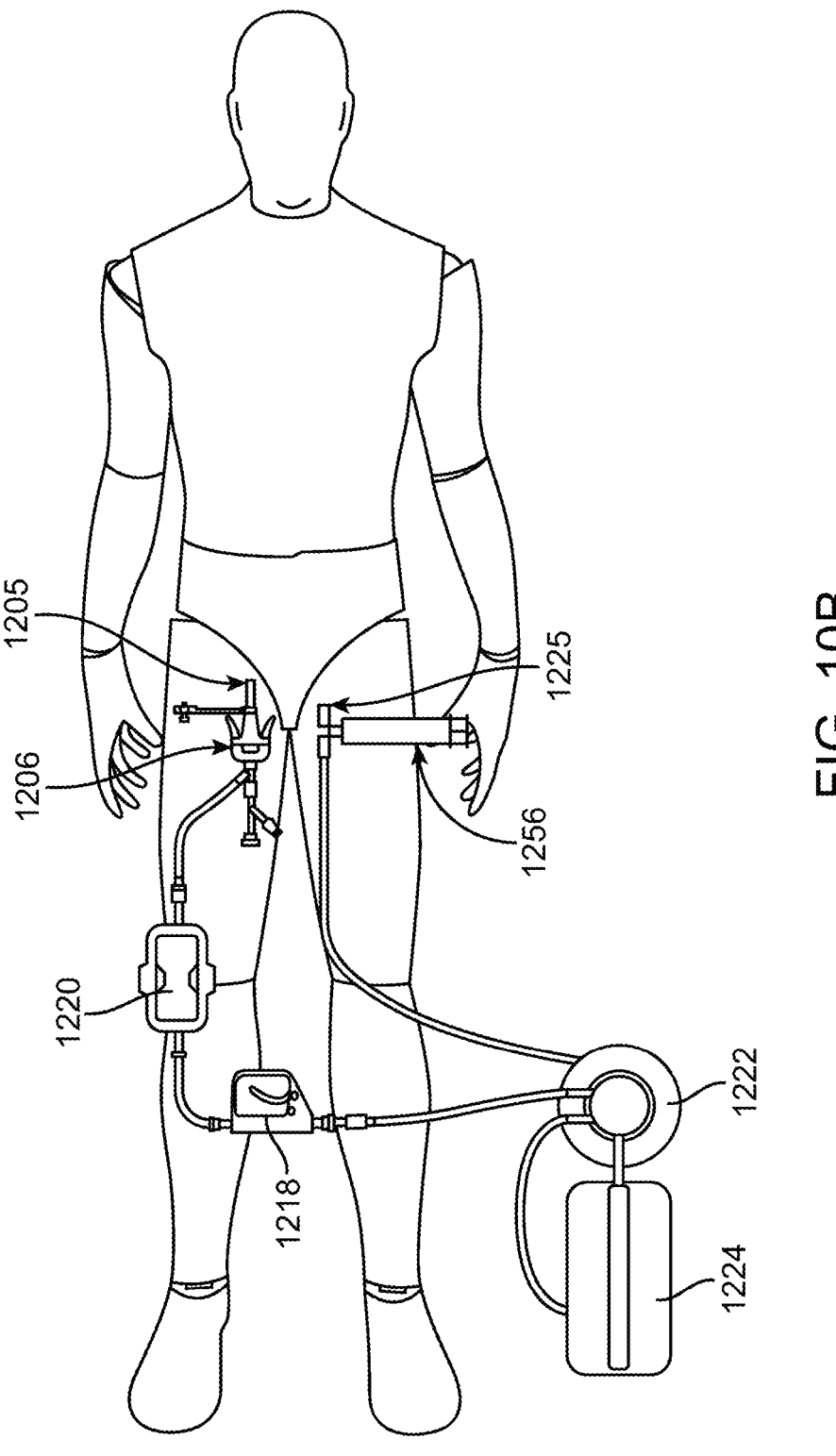

As mentioned, the order of the components of the blood circuit may be different. FIGS. 10A-10B show an example of a system in which the clot capture chamber 1220 positioned proximal to the suction valve 1218. For example, in FIG. 10A, the rigidizing aspiration sheath catheter and/or aspiration catheter 1791 may be proximal to the clot collection chamber 1792 which is proximal to the suction valve 1793 (e.g., shown as a hand valve 1218 in FIG. 10B) and the blood collection chamber (e.g., suction cannister) and pump 1794.

Figure 11A:
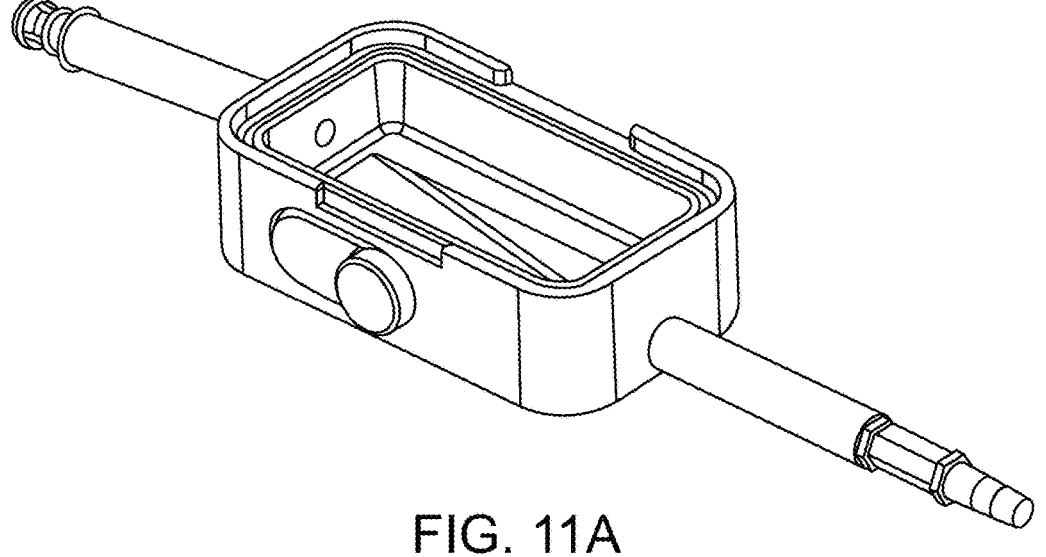
FIGS. 11A-11B illustrate an example of a clot capture chamber that is configured to reduce hemolysis.
Figure 11B:
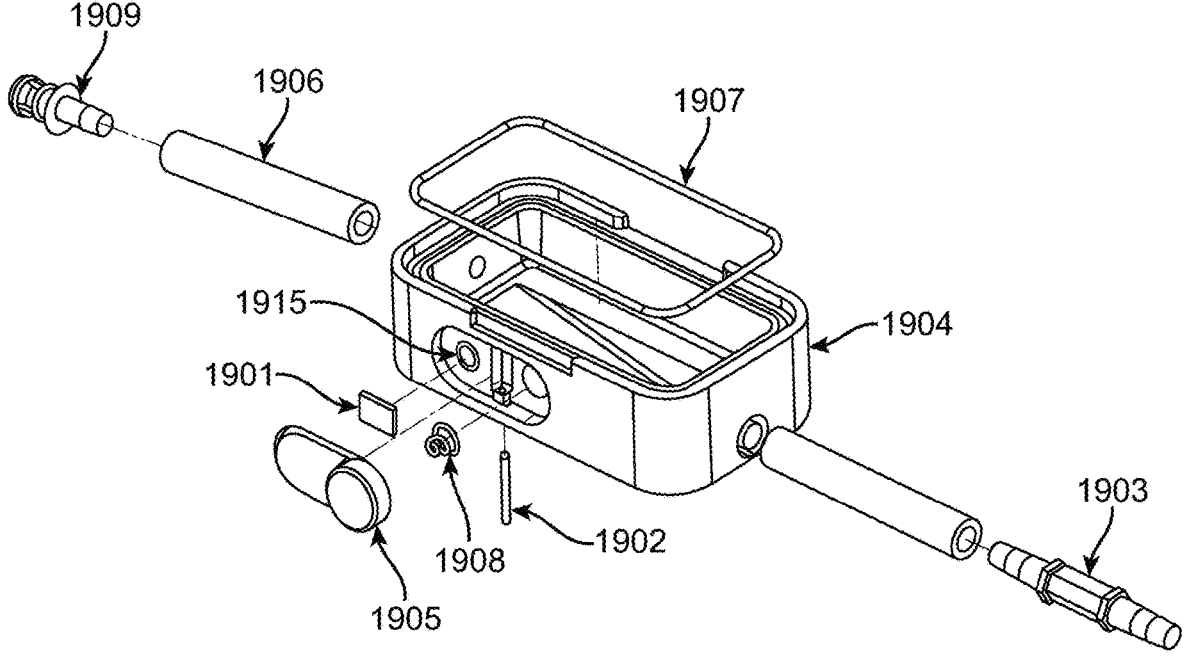

As mentioned, any of the systems described herein may include a clot capture chamber/container. The clot capture chamber may be configured to prevent or reduce hemolysis during the procedure. The clot capture chambers may be configured to infuse air into the clot capture chamber during venting at a control rate (e.g., more slowly/gradually than simply releasing/opening the system). This can be done by modulating diameter of hole beneath the venting button. FIGS. 11A-11B illustrate another example of a clot capture chamber 1900 configured to minimize hemolysis. In the example of FIGS. 11A and 11B, the clot capture chamber includes a common rotator seal 1901, a dowel pin 1902, a barb fitting 1903, a clot capture body 1904, a release (vent) button 1905, tubing 1906, o-ring 1907, a conical spring 1908, a barb fitting (male) 1909, and sealing connectors. By reducing diameter of the opening 1915 controlled by the button 1905, e.g., to a range of 0.020" to 0.100" slowed airflow in a way that reduces hemolysis.

Figure 12A:
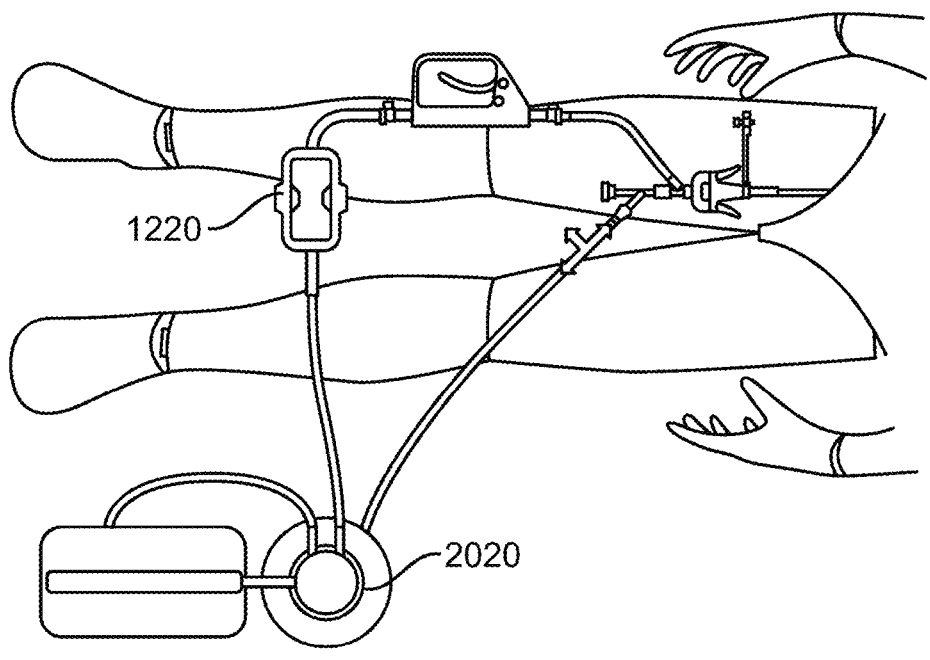
FIGS. 12A-12B illustrate an example of a system including a venting control (e.g., venting button) that may reduce hemolysis.
Figure 12B:
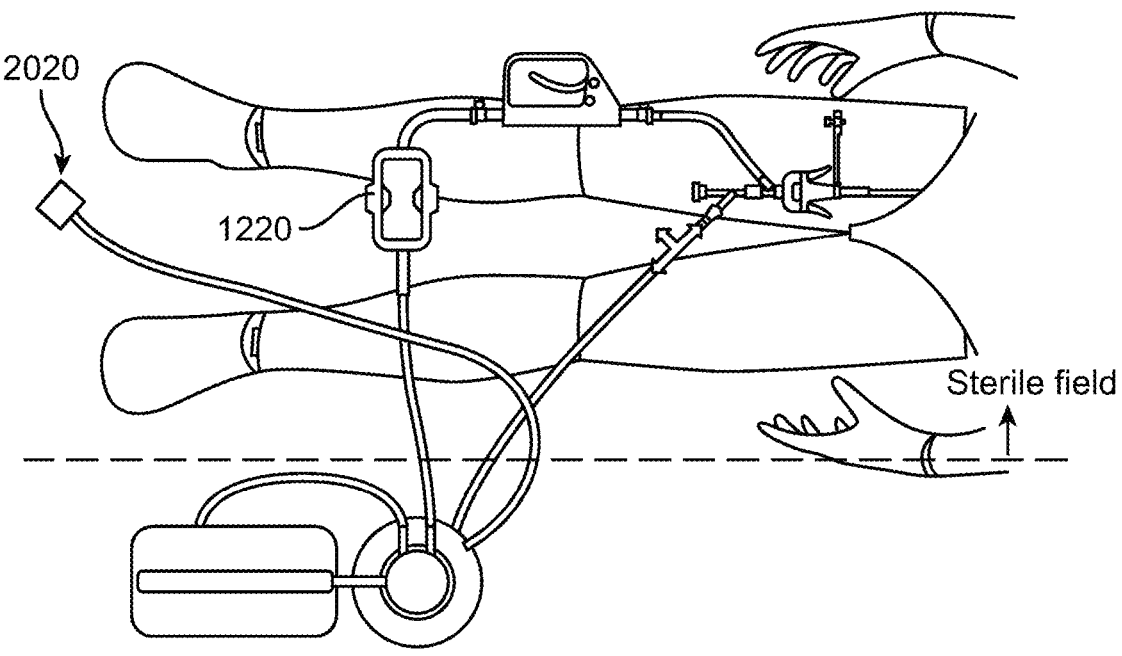

In any of these apparatuses a venting button may be positioned on top of the reservoir (e.g. the blood capture/filter chamber 1222). The venting button could be similar to the one shown in FIG. 11B in the clot capture chamber 1900, with an associated hole/orifice whose diameter is in the range of, e.g., 0.020" to 0.100". When it is time to eliminate vacuum from the interior this button 1905 may be pressed so that air leaks into top of blood capture/filter chamber 1222. This is illustrated in FIG. 12A. As a consequence, there would be no rushing of air and blood in the tubing. Some blood may stay behind in the clot capture device, but overall there should be a reduction in hemolysis. In some examples a tube may extend from the reservoir to the sterile field, and the vent button 2020 may be pressed on the sterile field, as illustrated in FIG. 12B.

Figure 13:
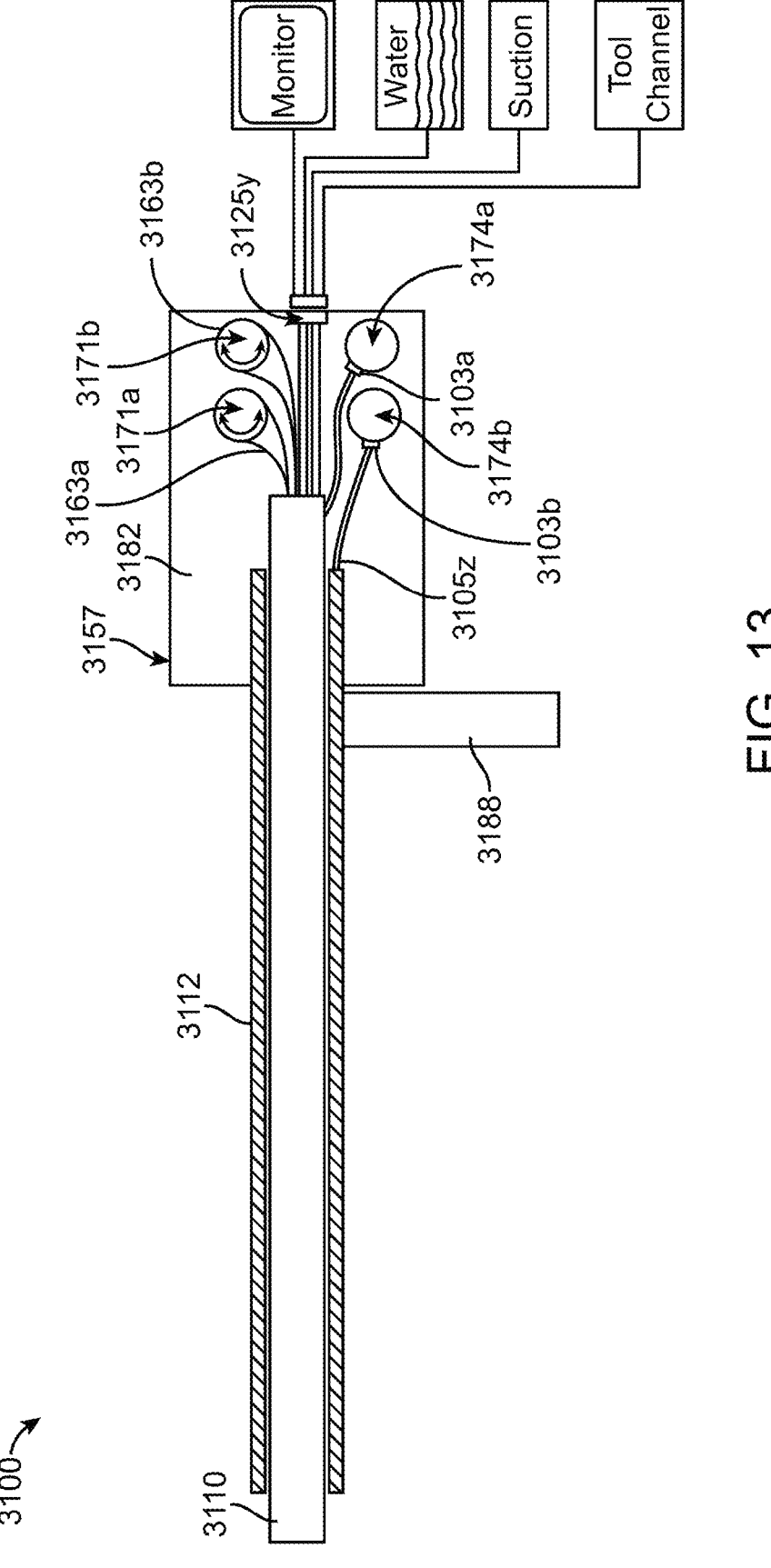
FIG. 13 illustrates an example of a robotic system including a rigidizing aspiration sheath catheter as described herein.

Any of the apparatuses described herein may be configured as part of a robotic system or for use with robotic apparatuses. In some examples the rigidizing aspiration sheath catheter system may include an outer tubular member that is robotically controlled, such as a robotically controlled overtube and/or endoscope assembly. FIG. 13 (not to scale) shows a schematic examples of an apparatus 3100 configured as a rigidizing aspiration sheath catheter system that may be robotically controlled. The rigidizing aspiration sheath catheter system may include an elongate flexible body having a plurality of layers, including a rigidizing layer and a bladder layer that is configured to transition the rigidizing layer between a flexible state and a rigid state, and a lumen extending through the elongate flexible body as described herein. The rigidizing aspiration sheath catheter may include a hemostasis valve region 3188 extending proximally from the elongate flexible body, the hemostasis valve region may include a housing having a central bore that is continuous with the lumen, and comprising an annular seal within the central bore and at least one actuator movable coupled to the housing and configured to open and close the annular seal or to seal around a device positioned within the central bore, wherein the at least one actuator is sized and shaped to be used by one hand of a user.

In the system 3100 in FIG. 13, the rigidizing aspiration sheath catheter may be configured as the outer 3112 or inner endoscope 3110. The overtube and inner endoscope can be separately or collectively be robotically controlled or manipulated (e.g., steering, movement, rotation, etc. including in some examples, rigidizing). As shown in FIG. 13, the outer overtube 3112 and the inner endoscope 3110 may be terminated together into a common structure, such as a cassette 3157. The outer overtube 3112 can be movable with respect to the endoscope 3110 by rotation of a driver mounted to the cassette 3157. The system may include actuators 3171a, 3171b that may connect to cables 3163a,b respectively, to steer (e.g., bend or deflect) the tip of the endoscope 3110 (and/or outer overtube 3112). Other steering mechanisms (e.g., pneumatics, hydraulics, shape memory alloys, EAP (electro-active polymers), or motors) are also possible. The cassette 3157 can further include bellows 3103a, 3103b that may connect to the pressure gap of the endoscope 3110 and the overtube 3112, respectively to drive fluid through pressure lines 3105z, in variations for either the endoscope and/or the overtube that are configured to rigidize when pressure is applied. As shown in this example, the cassette 3157 can include eccentric cams 3174a,b to control bellows 3103a,b. Alternatively, one or more linear actuators can be configured to actuate the bellows. As another alternative, the devices can be rigidized and de-rigidized through one or more pumps or pressure sources (e.g., via pressure line 3105z).

Figures 14, 15A:
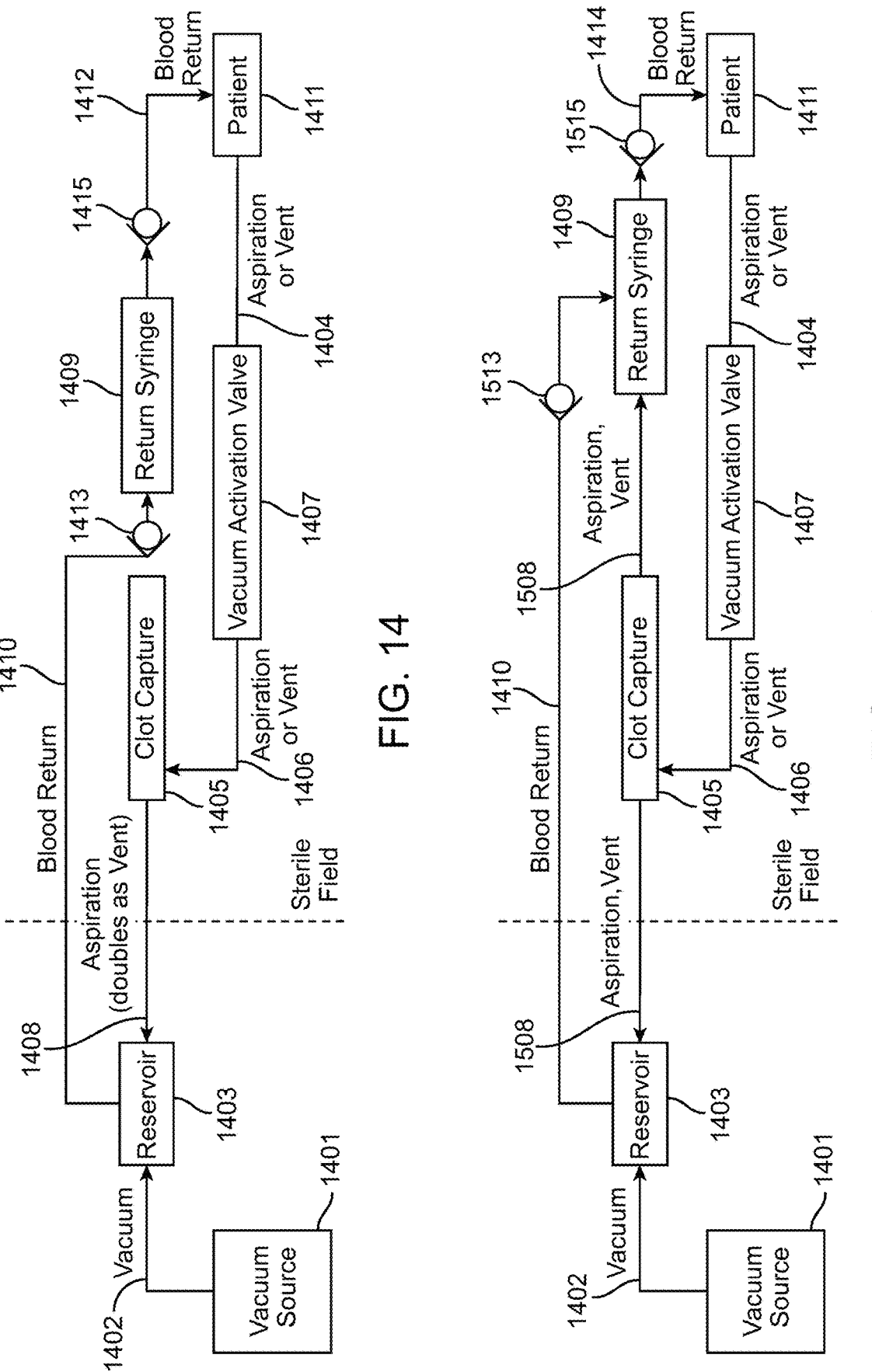
FIG. 14 illustrates a block diagram of an example blood return assembly as part of a clot aspiration system.
FIG. 15A illustrates a block diagram of another example blood return assembly.

FIG. 14 shows a block diagram of an example blood return assembly as part of a clot aspiration system. The diagram of FIG. 14 is a connection diagram showing how various components of the blood return assembly are connected. In this example, the system includes a vacuum source 1401, blood reservoir 1403, clot capture chamber 1405, vacuum activation valve 1407 and a blood return syringe 1409. The clot capture chamber 1405, vacuum activation valve 1407 and return syringe 1409 may be within a sterile field, while the reservoir 1403 and the vacuum source 1401 may be outside of the sterile field.

The vacuum source 1401 is in line with the reservoir 1403 (via a vacuum line 1402), the clot capture chamber 1405 (via an aspiration line 1408) and the vacuum activation valve 1407 (via aspiration line 1406). The vacuum activation valve 1407 controls the application of the vacuum (suction) to the patient 1411 via aspiration line 1404). The vacuum activation valve 1407 may be part of an aspiration catheter handle, as described herein. The aspirated blood from the patient 1411 travels from the vacuum activation valve 1407 through the clot capture chamber 1405, which is configured to capture at least some of the clot material. The clot capture chamber 1405 may also be configured to prevent or eliminate hemolysis of the blood, as described herein. The blood that passes through the clot capture chamber 1405 travels to the reservoir 1403. The reservoir 1403 may include one or more filters that are configured to filter the blood of any further blood clots and/or other debris, and be configured to temporarily store some of the filtered blood. The reservoir 1403 is connected to the blood return syringe 1409 via a blood return line 1410. A check valve 1413 may prevent blood from returning to the reservoir 1403 from the return syringe 1409. The blood return syringe 1409 is configured to inject the filtered blood into the patient 1411 via a blood return line 1412. A check valve 1415 may prevent blood from returning to the syringe 1409 from the patient.

As described herein, the return syringe 1409 may include a plunger and barrel. The plunger may be pulled back to draw blood into the barrel from the reservoir 1403. Before doing so, the pressure within the barrel of the syringe 1406 may need to be equalized with the pressure within the reservoir 1403. To do this, the lid of the clot capture chamber 1405 may be opened to the external atmosphere. As discussed herein, opening the lid of the clot capture chamber 1405 may include pressing clot capture vent valve (e.g., also referred to as a vent button) that allows the controlled infusion of air from an external atmosphere into the clot capture chamber 1405, thereby preventing or reducing hemolysis. Since the clot capture chamber 1405 is in line with the reservoir 1403 and the return syringe 1409, opening the clot capture chamber 1405 also vents the reservoir 1403 and the return syringe 1409, thereby equalizing the pressure between the reservoir 1403 and the return syringe 1409. Once the pressure is equalized, blood can be drawn into the syringe 1409 to charge the syringe 1409 for injection into the patient 1411. After the blood is injected into the patient, the lid of the clot capture chamber 1405 may be closed again so that blood can continue to be aspirated into the clot capture chamber 1405 from the vacuum activation valve.

FIG. 15A shows a block diagram of another example blood return assembly. FIG. 15A is a connection diagram showing how various components of the blood return assembly are connected. The blood return assembly of FIG. 15A is similar to the blood return assembly of FIG. 14 except that the blood return assembly of FIG. 15A includes a common vent line 1508 that is configured to fluidly couple the reservoir 1403, the clot capture chamber 1405 and the blood return syringe 1409. In addition, the return syringe 1409 includes a syringe vent valve (see, e.g., FIGS. 19A-19D) that is configured to allow venting of the blood return syringe to the common vent line 1508. Compared to the system of FIG. 14, these additional features allow for venting of the return syringe 1409 without needing to open the lid of the clot capture chamber 1405. For example, the syringe vent valve of the return syringe 1409 may be opened to vent the return syringe 1409 to the common vent line 1508, and the clot capture vent valve of the clot capture chamber 1405 may be opened to vent the clot capture chamber 1405 the external environment. This equalizes the pressure among the blood return syringe 1409, the clot capture chamber 1405 and the reservoir 1403, thereby allowing the blood to be drawn into the syringe 1409 for injection into the patient 1411. In this way, the common vent line 1508 and the syringe vent valve of the return syringe 1409 can allow for a streamlined workflow during the clot aspiration and blood return procedure.

In addition, this provides a dedicated vent line 1508 may reduce the amount of hemolysis when the clot capture chamber 1405 is vented since the reservoir 1403 no longer needs to be vented through the column of blood in line between clot capture chamber 1405 and reservoir 1403. Venting directly results in a lower reservoir pressure when blood is drawn into the reservoir 1403, therefore it can be done in a much less vigorous manner.

Figure 15B:
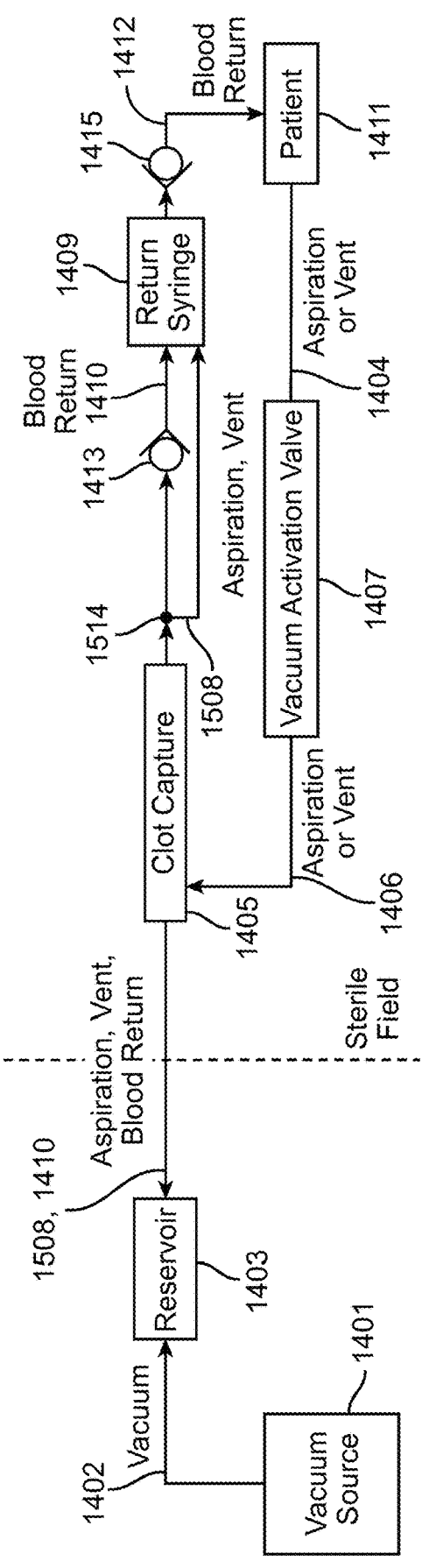
FIG. 15B illustrates an example simplified routing diagram of the blood return system of FIG. 15A, showing how tubing may be bundled together for streamlining.

FIG. 15B is an example simplified routing diagram of the blood return system of FIG. 15A, showing how tubing may be bundled together for streamlining. The aspiration, vent and blood return lines 1508, 1410 (which may be three separate lines/tubes) may be bundled together at the clot capture chamber 1405 in order to simplify the tubing arrangement. The syringe vent valve 1514 can be configured to open the return syringe 1409 to the common vent line 1508 (e.g., when venting the syringe 1409 for filling with blood) or close the return syringe 1409 to the common vent line 1508 (e.g., when using the syringe 1409 to inject blood into the patient). Bundling of tubing between components can make the system more organized (e.g., on a table). Routing of the return line through clot capture chamber 1405 can serve the same goal as it can be bundled with the vent line from the reservoir 1405 all the way to the syringe 1409.

Figure 15C:
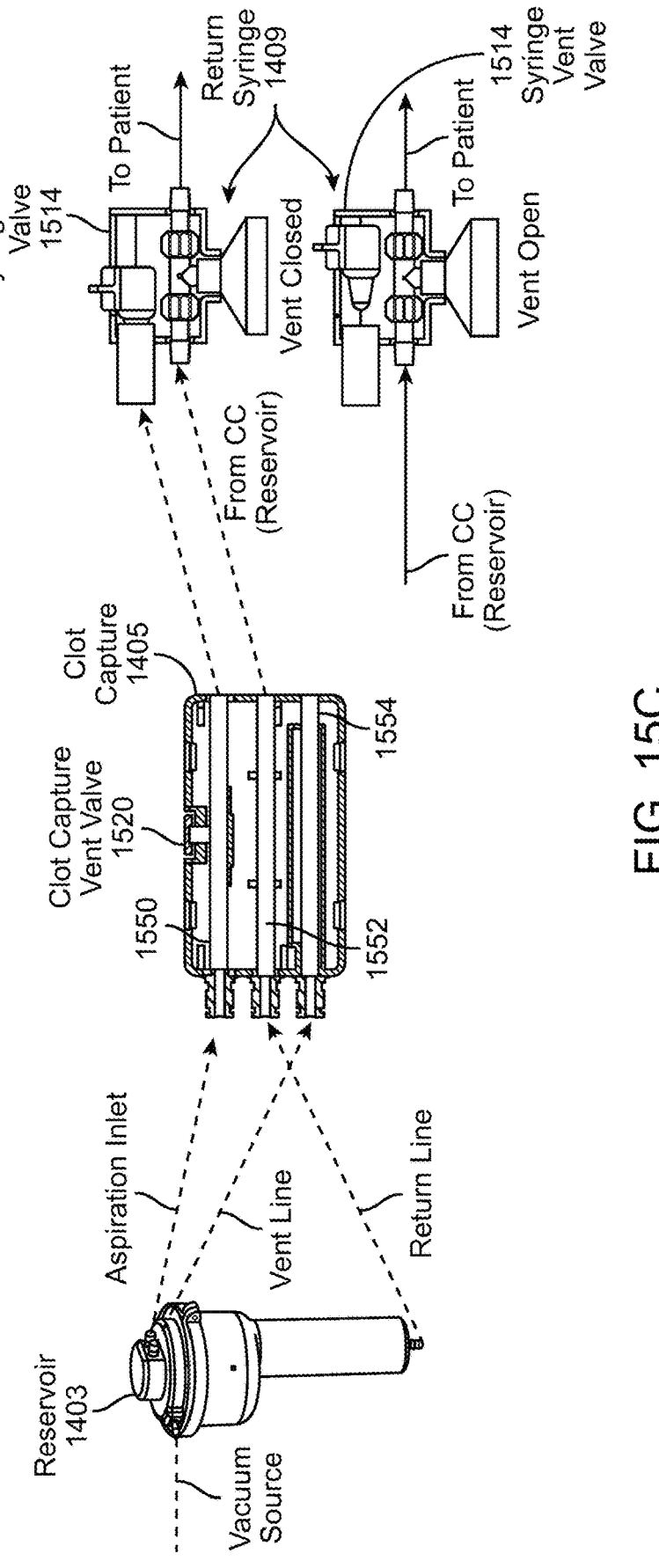
FIG. 15C illustrates example details of the tube routing through the clot capture chamber of the blood return system of FIG. 15A.

FIG. 15C shows example details of the tube routing through the clot capture chamber 1405. In this example, the clot capture chamber 1405 includes a first connector 1550, a second connector 1552, and a third connector 1554. The connectors (or channels) 1550, 1552 and 1554 may correspond to groves and/or notches on or within the clot capture chamber 1405 and that are configured to secure corresponding tubing. In this example, the first connector 1550 is configured to secure the aspiration line (tubing) for carrying aspirated blood from the clot capture chamber 1405 to the reservoir 1403; the second connector 1552 is configured to secure the return blood line (tubing) for carrying filtered blood from the reservoir 1403 to the return syringe 1409; and the third connector 1552 is configured to secure the common vent line (tubing). The aspiration line and the vent lines may be switched between connectors 1150 and 1554 without affecting performance.

As discussed earlier, the clot chamber vent valve 1555 can be configured to vent the clot capture chamber 1405 to the external environment. The clot chamber vent valve 1555 may be in a normally closed position and activated (e.g., by pushing) to open (e.g., momentarily) to the surrounding atmosphere. The syringe vent valve 1514 (shown in closed and open positions) is configured to vent the return syringe 1409 to the common vent line 1508.

Figures 16A, 16B, 16C:
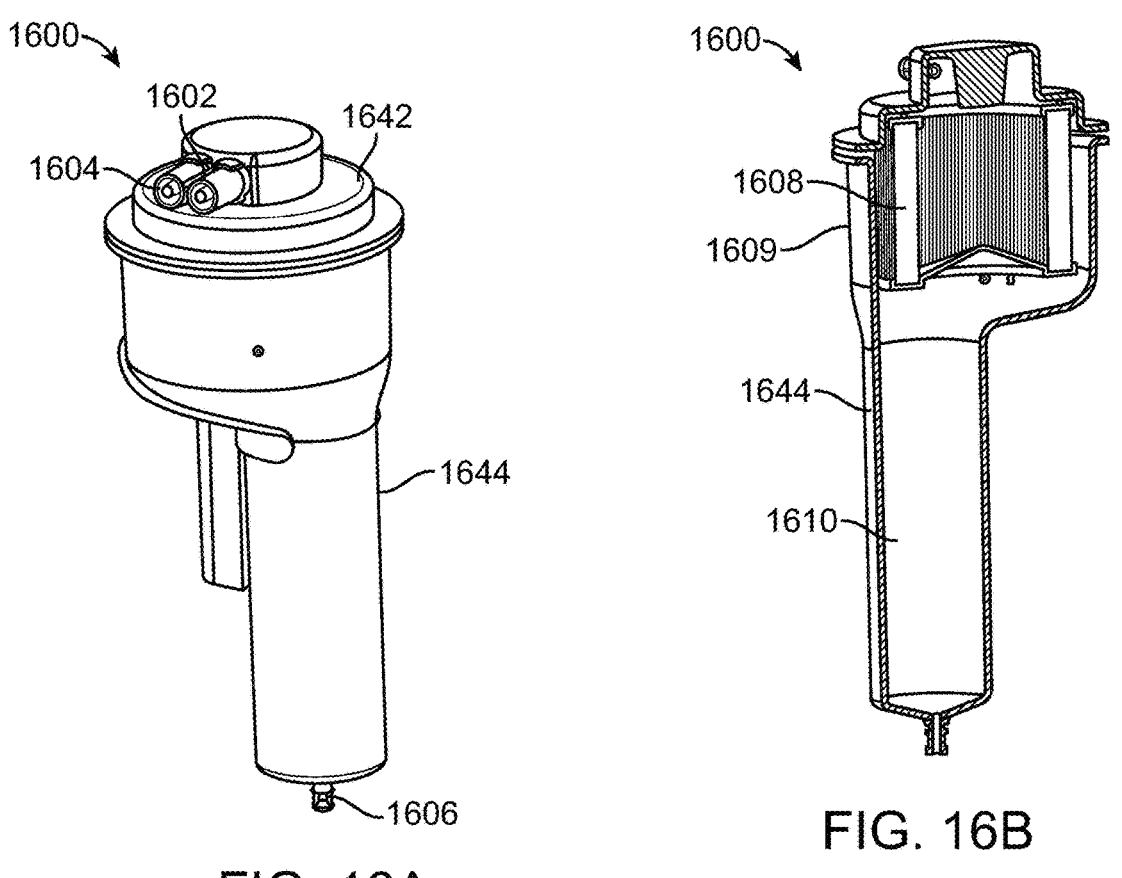
FIGS. 16A-16C illustrate various views of an example blood reservoir.
Figure 17A:
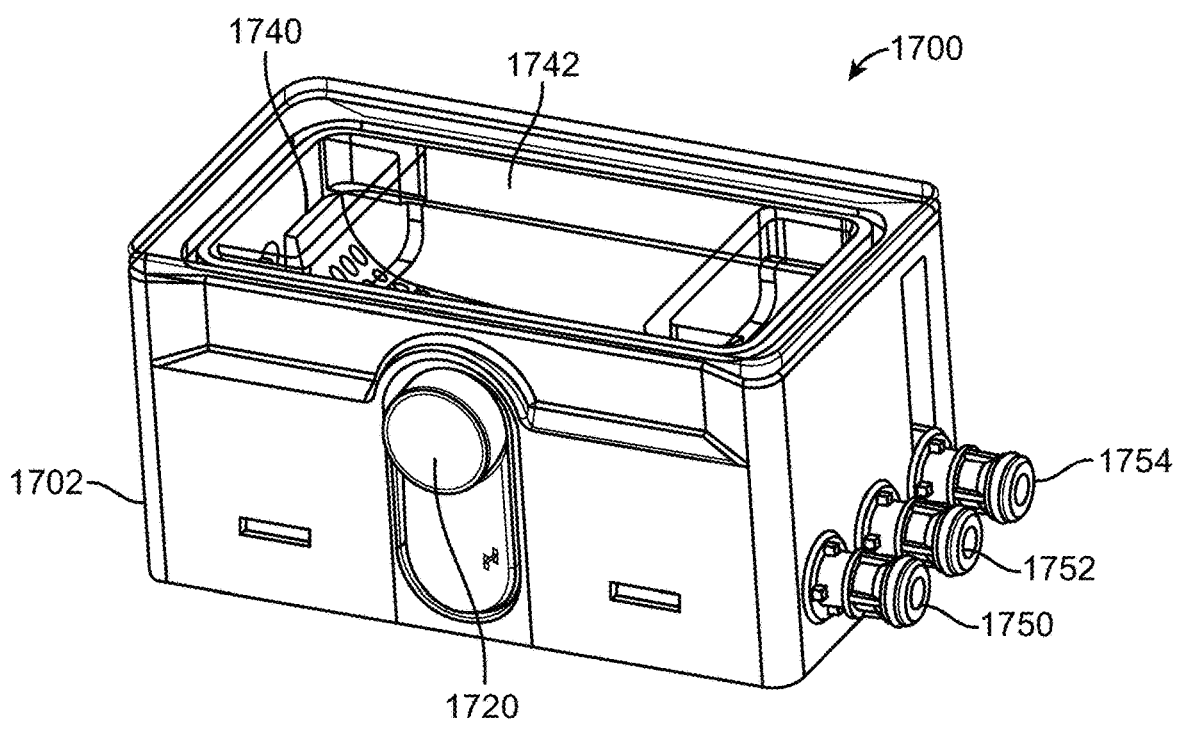
FIGS. 17A-17D illustrate various views of an example clot capture chamber.
Figure 17B:
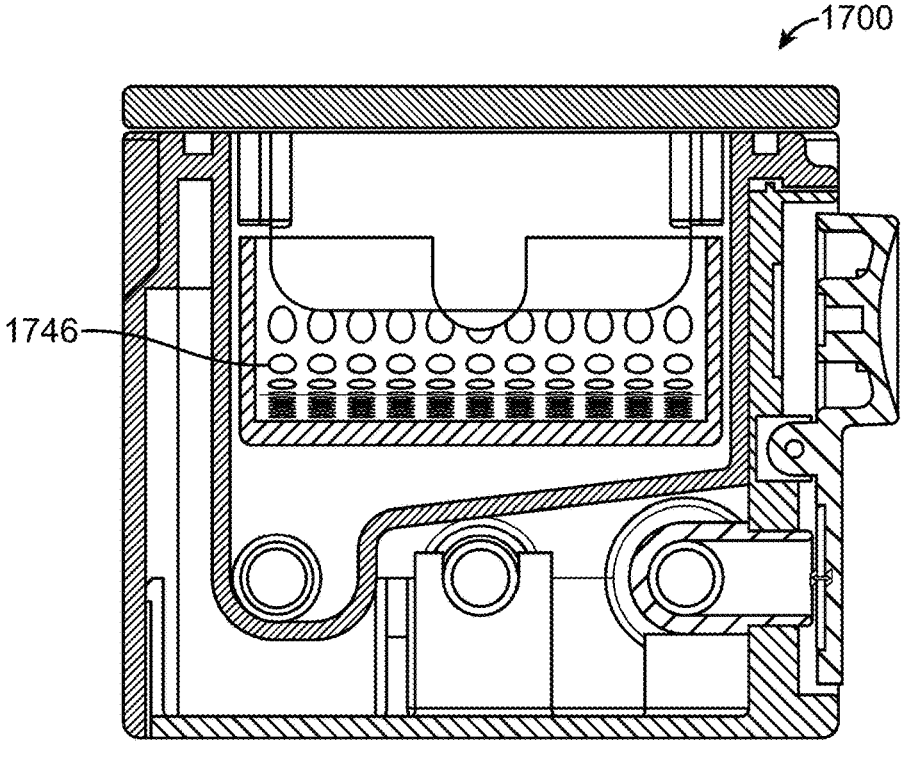
Figure 17C:
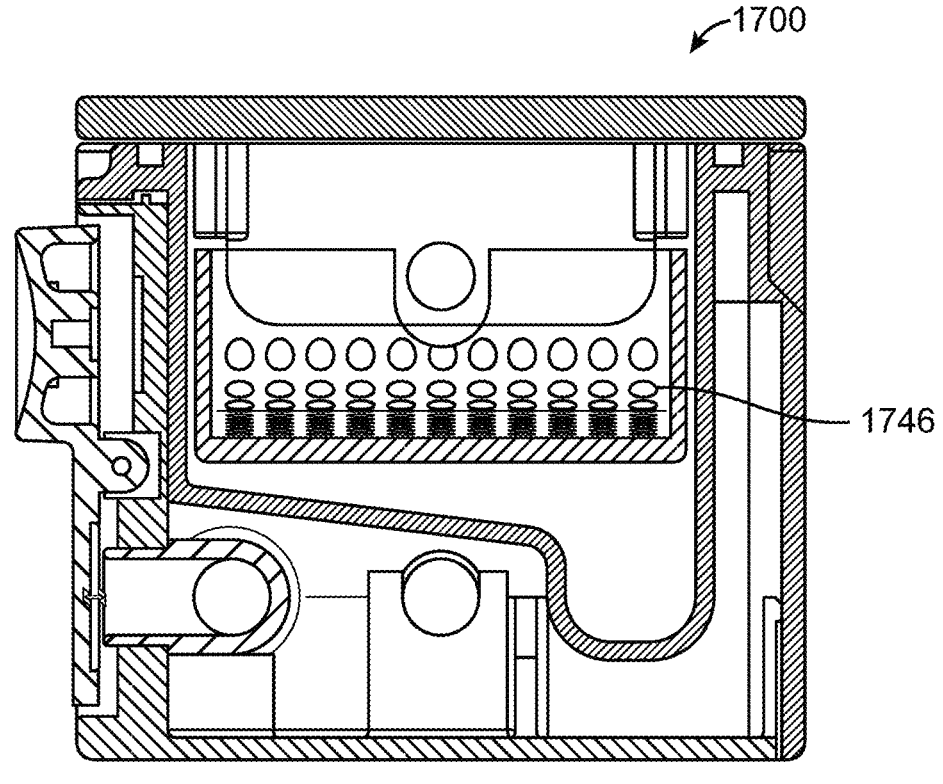
Figure 17D:
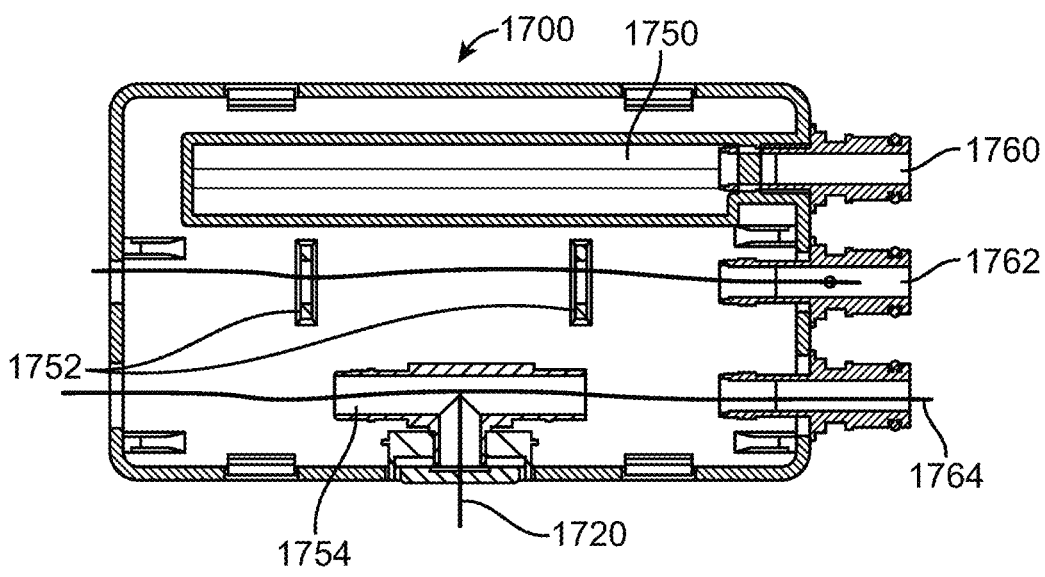

FIGS. 16A-16C show various views of an example reservoir 1403. The reservoir 1600 includes lid 1642 that is removably coupled to a container portion 1644. In this example, the lid 1642 includes a first port 1602 that may be configured to connect to an aspiration line for accepting blood into the reservoir 1600 (e.g., from the clot capture chamber); a second port 1604 that may be configured to connect to a vent line to vent the reservoir 1600; and a third port 1606 that may be configured to connect to a blood return line (e.g., to the blood return syringe).

The container portion 1644 defines an upper chamber 1609 that houses a filter assembly 1608, which is configured to filter blood entering the reservoir 1600 to remove remaining clot material and/or other debris from the blood. The container portion 1644 also defines a lower chamber 1610 that is configured to capture and temporarily store the filtered blood until it exits the lower chamber 1610 via the third port 1606—in this case, at the bottom of the reservoir 1600.

At least a portion of the container portion 1644 can be visually transparent (e.g., "sightglass") so that a user may visualize a current blood level in the reservoir 1600. Since the reservoir 1600 may be outside of the sterile field during the clot aspiration procedure, the sightglass feature may allow a user to visualize, from a distance, how much blood has been removed from the patient and collected in the reservoir 1600 has been removed from the patient and stored in the reservoir 1600 so that the user can have a quick estimation of fluid level. The reservoir 1600 may include graduation marks (e.g., in cubic centimeters (cc)) that can help the user estimate the amount of blood within the reservoir 1600.

FIGS. 17A-17D show various views of another example of a clot capture chamber 1700. The clot capture chamber 1700 includes a removable tray 1740 that includes an intermediate surface 1746, which is configured to capture blood clot material and includes perforations to let blood flow through to a lower portion of the clot capture chamber 1700. In some cases, the intermediate surface is sloped relative to a bottom surface of the clot capture chamber 1700 when the removable tray 1740 is within the clot capture chamber 1740, which can improve efficiency of flow and reduce clogging of the perforations.

A transparent lid 1742 allows a user to view the contents of the removable tray 1740 without opening the lid 1742. The lid 1742 may include handles for easy removal and placement. When under negative pressure from an attached vacuum source, the lid 1742 may be sealed to the container 1702. To enable opening of the lid 1742, a user may press a vent control button 1720 to vent the container 1702 to atmosphere and to release the negative of pressure within the container 1702.

In this example, the clot capture chamber 1700 includes a first port 1760 and a first connector 1750 that is configured to connect with an aspiration line (tubing) for carrying aspirated blood from the clot capture chamber 1700 to the reservoir; second port 1762 and a second connector 1752 that is configured to connect with the blood return line (tubing) for carrying filtered blood from the reservoir to the return syringe; and a third port 1764 and a third connector 1752 that is configured to connect with the common vent line (tubing). In this example, the first connector 1752 is a channel that provides fluid access to the container 1702 so that blood that passes through the perforations of the tray 1740 can flow to the reservoir; the second connector 1752 includes fasteners that secures the tubing for the blood return line (i.e., does not allow blood to flow through the container

1702 of the clot capture chamber 1700); and the third connector 1754 is channel that provides fluid access to the surrounding atmosphere via the vent control button 1720.

Figure 18A:
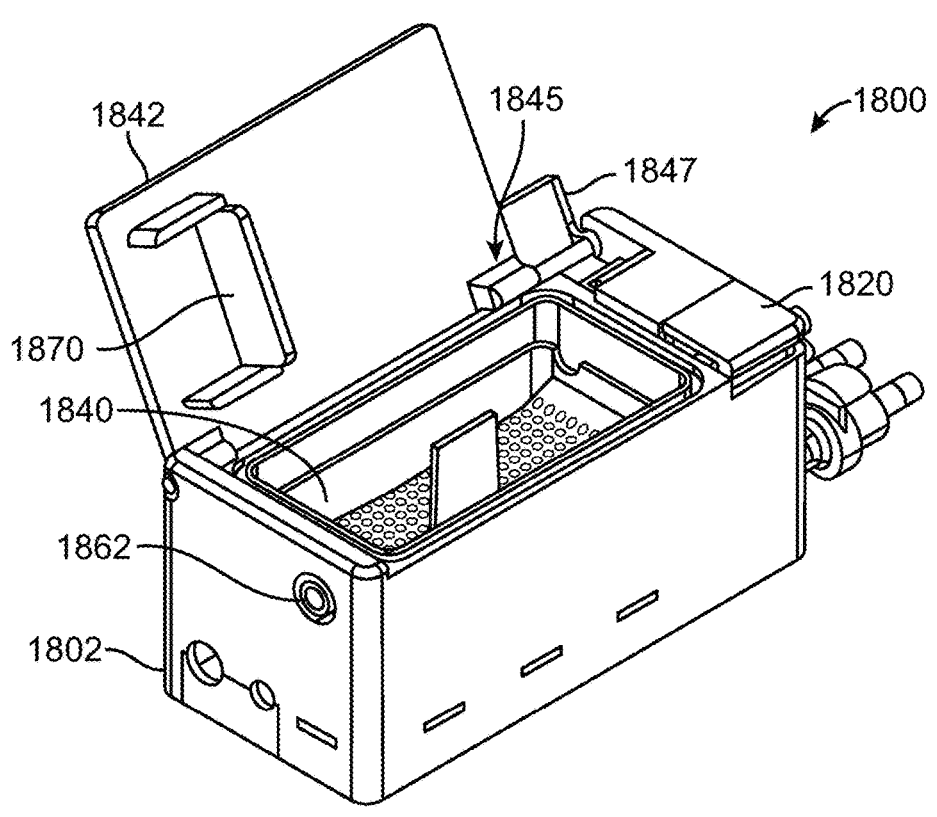
FIGS. 18A and 18B illustrate another example of a clot capture chamber.
Figure 18B:
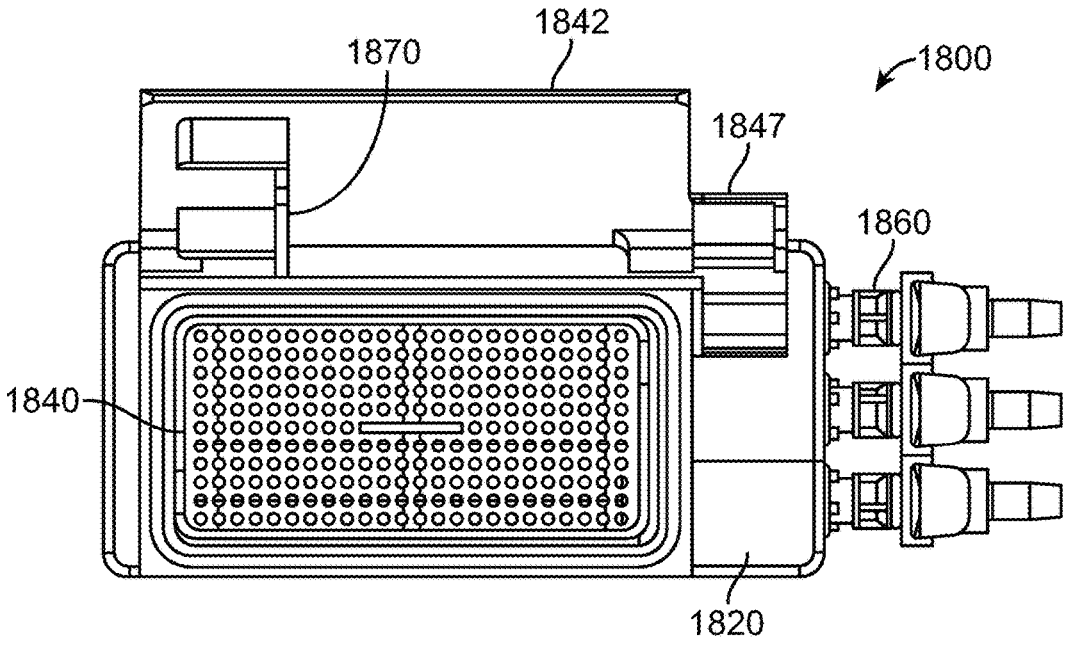

FIGS. 18A and 18B show a further example of a clot capture chamber 1800. The clot capture chamber 1800 has some similar features as the clot capture chamber 1700. For example, as with the lid 1742 of the clot capture chamber 1700, at least a portion of the lid 1842 of clot capture chamber 1800 is visually transparent so that the user can visualize the inside of the clot capture chamber 1800. In this example, the lid 1842 is connected to the container 1802 by a hinge assembly 1845 that includes a spring that spring loads the lid 1842. So long as a clot capture vent button 1820 is pressed, the vacuum force within the clot capture chamber 1800 becomes low enough such that the lid 1842 automatically opens. When the lid 1842 opens, the user can then use one hand to retrieve the tray 1840, for example, to inspect the clot material.

When the user wants to close the lid 1842, they can push the lid 1842 down and the lid 1842 remains in the closed position by a latch 1847 of the hinge assembly 1845. In this example, the latch 1847 includes a snap feature that is configured to hold the lid 1842 in a closed position and to move out of the way to allow the lid 1842 to spring open. The latch 1847 can hold the lid 1842 down, for example, when the user opens the syringe vent valve of the blood return syringe. This allows the lid 1842 to be open only when the clot capture vent button 1820 is pressed and the latch 1847 is moved out of the way.

The lid 1842 also includes a wall 1870 that is arranged near a blood inlet 1862 that allows blood to flow into the clot capture chamber 1800 via the aspiration line from the aspiration catheter (e.g., from the vacuum activation valve 1407 in FIGS. 14, 15A, 15B). The wall 1870 can prevent the incoming blood from splattering on a remainder of the lid 1842 so that the user can see through the transparent lid 1842. In addition, the wall 1870 may reduce the occurrence of hemolysis.

The clot capture chamber 1800 may also include a one-way valve (check valve) to the aspiration line 1860. This is a solution to an artifact of pressing the vent button 1820, and the blood that is in the line between the clot capture chamber 1800 and the reservoir can flow down into the clot capture chamber 1800, flooding it with blood. The one-way valve prevents this flowing back of blood, ensuring good visibility of the clot material within the clot capture chamber 1800.

Figures 19A, 19B, 19C, 19D:
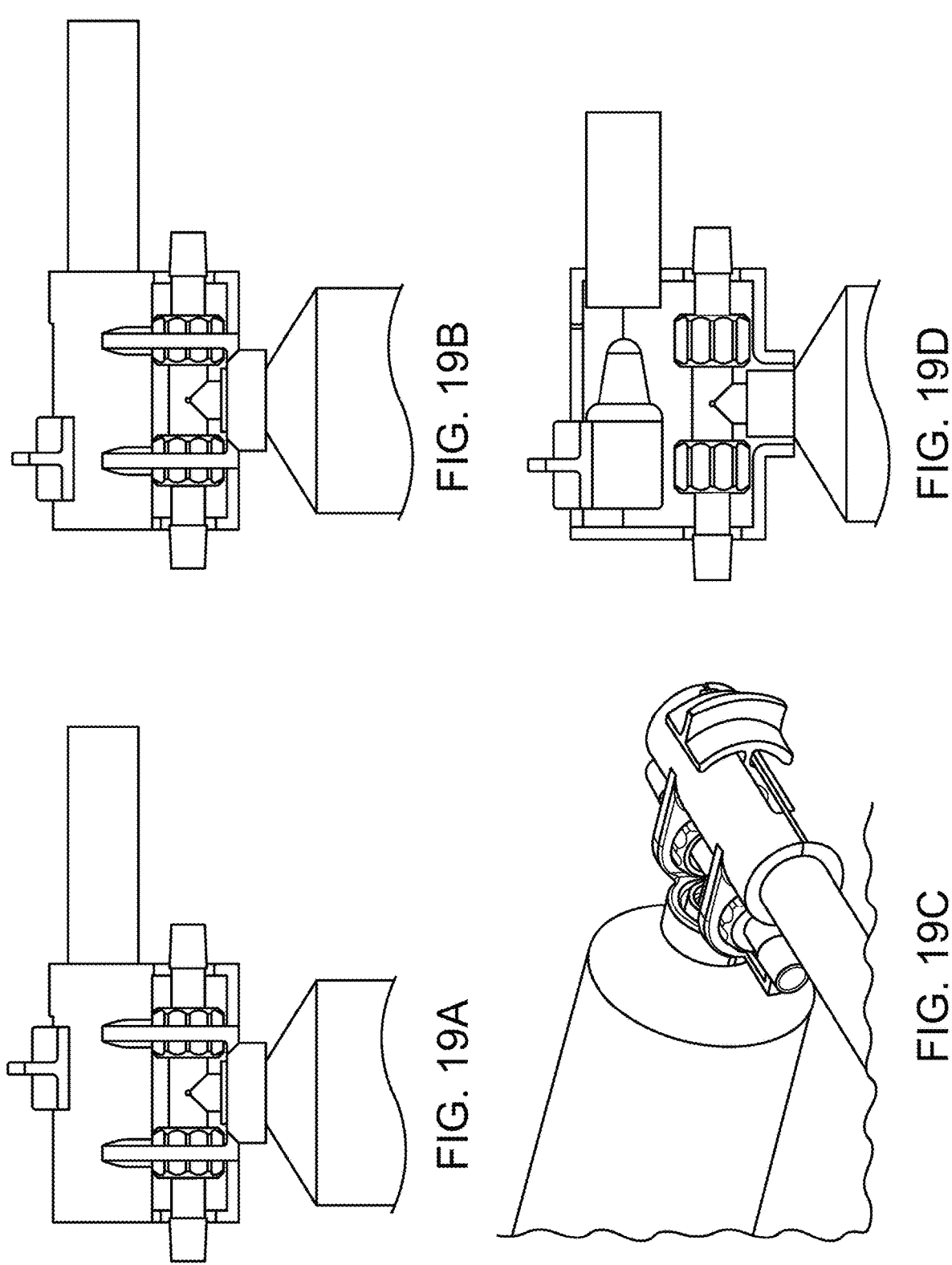
FIGS. 19A-19D illustrate an example of a syringe vent valve of a blood return syringe.

FIGS. 19A-19D show various views of an example syringe vent valve of a blood return syringe. FIGS. 19A and 19C show the syringe vent valve in a closed position so that the system can aspirate blood as described above. FIGS. 19B and 19D show the syringe vent valve in an open position, venting the aspiration line, so that the user can reinfuse blood into the patient as described above. For example, by pumping blood from the blood capture container (e.g., see FIGS. 16A-16C) into a syringe and from the syringe into the patient.

EXAMPLES

Described herein are methods and apparatuses for removing a pulmonary embolism with a minimally invasive catheter approach (rather than an open pulmonary thromboendarterectomy), using the rigidizing apparatuses in combination with an aspiration catheter. As described above, in general the physician may start in a femoral vein and following the twists and turns of the vasculature up and through the right atrium, then the right ventricle and into the pulmonary artery. This may result in high blood pressure risks damage to the heart and vasculature, particularly with relatively rigid catheters, as are often required by the prior art, such as currently used large-bore, stiff catheters, which may distort the anatomy, and may be difficult to control. Such systems may require multiple guidewire exchanges position the catheters, for example, a soft-wire guide catheter, which may be swapped for a stiffer wire, and may use a separate guide catheter to insert the treatment catheter. In addition to taking time, such systems may lose positioning, requiring multiple repetitions of the positioning technique, further increasing stress on the heart and vasculature. In contrast, the methods described herein may require significantly fewer guide wire swaps and device swaps, as well as substantially less repositioning, as the rigidizing catheter may be positioned while in an extremely pliant (e.g., flexible) configuration using a single, e.g., soft, guidewire, and may be made rigid once positioned, to provide a stable platform from which the aspiration catheter may be extended and guided, in a manner that is not possible with current systems.

FIG. 20A illustrates one example of an apparatus (e.g., system) 2010 as described herein, including an aspiration catheter 2003 with an integrated hemostatic valve 2026 and a flush port 2035. The aspiration catheter couples to a distal end of vacuum line 2017 with a hand-triggered vacuum activation valve 2018 is shown connected in-line with the vacuum line and may be easily used to turn on/off suction through the apparatus. The vacuum line is also connected to a clot capture chamber 2020, examples of each of which are described above. The suction catheter 2003 is inserted through a second hemostasis valve 2025 at the proximal end of the rigidizing catheter 2002 (which may also be referred to as a rigidizing aspiration sheath catheter).

FIGS. 20B and 20C illustrate examples of the nested outer rigidizing catheter 2002 and the inner aspiration catheter 2003. In the example shown the outer rigidizing catheter may be, for example, between 10F and 30F (e.g., 24F, 25F, 26F, 27F, 28F, 29F, etc.) or more. The inner aspiration catheter may be configured to fit within and slide relative to the outer rigidizing catheter. For example, the inner aspiration catheter may be between 5F and a 26F (e.g., between 10F and 24F, such as 18F, 19F, 20F, 21F, etc.). In operation, the outer rigidizing catheter may be converted between a relaxed and flexible state (which may be the unpressurized state) that is highly flexible and configured to track directly over a guidewire. In some cases a very flexible obturator may be used in combination with the guidewire, as described above, to enhance tracking with the guidewire without significantly reducing the flexibility. Once the rigidizing outer catheter is in position it can be rigidized, e.g., by applying positive and/or negative pressure as described above, e.g., in some cases using a locking insufflator and saline (the saline may provide hydrostatic pressure when applying positive pressure). When activated, the pressure is fully contained within the walls of the rigidizing catheter without causing any significant radial expansion of the catheter, and without changing shape (e.g., without elongating or foreshortening). Once locked into position, the outer rigidizing catheter may be multiple orders of magnitude more rigid than in the flexible configuration and may be maintained in this rigid state until it is desired to move the rigidizing catheter by removing the pressure (e.g., depressurizing the catheter), transitioning to the flexible configuration.

For example, as shown in FIG. 20B, the outer rigidizing catheter 2014 is shown in a rigid configuration; once rigidized, the inner aspiration catheter may be inserted and may navigate through the vasculature, including the heart, without applying further force against the vasculature or heart as the rigid outer catheter 2014 prevents the inner aspiration catheter 2003 from contacting and applying force as it passes through the body.

In any of these apparatuses the inner catheter 2003 may be relatively flexible over all or most of its length. For example, the inner aspiration catheter may be highly flexible along its proximal length, as the rigidizing outer catheter, in the rigid configuration, may allow it to be advanced distally through extremely long and tortious anatomy (e.g., greater than 0.3 m, greater than 0.4 m, greater than 0.5 m, greater than 0.6 m, greater than 0.7 m, greater than 0.8 m, greater than 0.9 m, greater than 1 m, greater than 1.1 m, etc.) while preventing kinking or bending.

In some cases the distal end of the inner aspiration catheter may be pre-bent or curved (e.g., shape set) to have a bend 2014, as shown in FIG. 20C, which illustrates an example of the clot-sucking end of the aspiration catheter. This biased distal end region may assume a curved shape when extended distally from the rigidizing outer catheter, and the inner aspiration catheter may be steered by torquing (rotating) the inner aspiration catheter relative to the outer rigidizing catheter. The inner aspiration catheter may be formed of a low-durometer elastomeric material and in some cases may include a stainless steel wire, e.g. for coil, wire-and/or braid-reinforced tubes. In some cases the inner aspiration catheter may be formed of a laser-cut hypotube, that may be formed to have a relatively high flexibility.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A blood clot aspiration system, comprising:
an aspiration catheter configured to aspirate blood from a patient's vasculature;
a clot capture chamber configured to receive the aspirated blood from the aspiration catheter and to capture and contain at least some blood clots from the blood;
a reservoir configured to receive blood from the clot capture chamber, wherein the reservoir includes a filter that is configured to filter the blood received from the clot capture chamber;
a blood return syringe configured to receive filtered blood from the reservoir and to inject the filtered blood into the patient's vasculature; and
a vent system comprising:
a common vent line that is configured to fluidly couple the reservoir, the clot capture chamber and the blood return syringe;
a syringe vent valve configured to allow venting of the blood return syringe to the common vent line to equalize a pressure among the blood return syringe, the clot capture chamber and the reservoir; and
a clot capture vent valve configured to allow venting of the clot capture chamber to an external atmosphere; wherein the clot capture chamber includes a lid that is spring-loaded to automatically open the lid when the clot capture chamber is vented to the surrounding environment.

2. The system of claim 1, further comprising a blood return line that is configured to carry filtered blood from the reservoir to the blood return syringe.

3. The system of claim 2, wherein the clot capture chamber includes a connector that is configured to physically couple to the clot capture chamber with the blood return line, wherein the clot capture chamber is not directly fluidly coupled with the blood return line.

4. The system of claim 3, wherein the clot capture chamber is coupled with the aspiration catheter via a catheter aspiration line.

5. The system of claim 4, wherein the clot capture chamber includes a first connector that is configured to physically couple the common vent line with the clot capture chamber, and a third connector that is configured to physically couple the catheter aspiration line with the clot capture chamber.

6. The system of claim 1, wherein the aspiration catheter includes a vacuum activation valve configured to allow the aspirated blood to flow into the clot capture chamber from the from the aspiration catheter, wherein the vacuum activation valve is configured to control suction through a lumen of the aspiration catheter.

7. The system of claim 1, wherein at least a portion of the reservoir is visually transparent so that a user can visualize a level of filtered blood contained within the reservoir.

8. The system of claim 1, wherein when the syringe vent valve is open, the blood return syringe is configured to draw filtered blood from the reservoir.

9. The system of claim 1, wherein the clot capture chamber includes a removable tray that includes an intermediate surface with a plurality of apertures and that is configured to capture blood clot material and allow unclotted blood to pass, wherein an intermediate surface is sloped relative to a bottom surface of the clot capture chamber when the removable tray is within the clot capture chamber.

10. The system of claim 1, wherein the clot capture chamber includes a latch that is configured to hold the lid in a closed position.

11. The system of claim 1, wherein the clot capture chamber includes a one-way valve that is configured to prevent blood from flowing back into the clot capture chamber from the reservoir when the clot capture chamber is vented to the external atmosphere.

12. The system of claim 1, wherein the aspiration catheter includes a rigidizing sheath comprising an elongate flexible body, the elongate flexible body comprising a plurality of layers, including a rigidizing layer and bladder layer that is configured to transition the rigidizing layer between a flexible state and a rigid state.

13. A method for removing blood clot material, the method comprising:
aspirating blood with the blood clot material from a patient's vasculature using an aspiration catheter, wherein:
a clot capture chamber receives the aspirated blood from the aspiration catheter and captures at least some of the blood clot material from the aspirated blood within the clot capture chamber;
a reservoir receives blood from the clot capture chamber, wherein the reservoir includes a filter that is configured to filter the blood received from the clot capture chamber;
opening a syringe vent valve to allow venting of a blood return syringe to a common vent line that fluidly couples the reservoir, the clot capture chamber and the blood return syringe, wherein opening the syringe vent valve equalizes a pressure among the blood return syringe, the clot capture chamber and the reservoir;
drawing filtered blood into the blood return syringe from the reservoir while the syringe vent valve is open;
injecting the filtered blood into the patient's vasculature from the blood return syringe; opening a clot capture vent valve to allow venting of the clot capture chamber to an external atmosphere, and opening a lid of the clot capture chamber to allow access to a removable tray, wherein the removable tray is configured to capture clots therein, wherein the lid automatically opens upon actuation of the clot capture vent valve.

14. The method of claim 13, further comprising closing the lid, wherein a latch of the clot capture chamber retains the lid in a closed position.

15. The method of claim 13, wherein the clot capture chamber includes one-way valve that prevents blood from flowing back into the clot capture chamber from the reservoir when the clot capture chamber is vented to the external atmosphere.

16. The method of claim 13, wherein the reservoir has a window that allows visualization of a level of filtered blood contained within the reservoir.

17. The method of claim 13, wherein aspirating the blood with the blood clot material from a patient's vasculature comprises:
advancing a rigidizing aspiration sheath catheter in the patient's vasculature while the rigidizing aspiration sheath catheter is in a flexible state so that a distal end of the rigidizing aspiration sheath catheter is near the blood clot material;

transitioning the rigidizing aspiration sheath catheter from the flexible state to a more rigid state; and aspirating through the rigidizing aspiration sheath catheter in the more rigid state.

18. The method of claim 17, wherein a proximal end of the rigidizing aspiration sheath catheter comprises a hemostasis valve portion.

19. The method of claim 17, further comprising:

inserting the aspiration catheter through the rigidizing aspiration sheath catheter;

extending the aspiration catheter distally out of the rigidizing aspiration sheath catheter proximate to the clot material with the rigidizing aspiration sheath catheter in the more rigid state; and aspirating through the aspiration catheter.

20. The method of claim 17, wherein transitioning the rigidizing aspiration sheath catheter from the flexible state to a more rigid state comprises applying pressure to one or more layers of the rigidizing aspiration sheath catheter.

* * * * *